United States Patent [19]
Sims et al.

[11] Patent Number: 6,100,443
[45] Date of Patent: *Aug. 8, 2000

[54] UNIVERSAL DONOR CELLS

[75] Inventors: Peter J. Sims, Mequon, Wis.; Alfred L. M. Bothwell, Guilford, Conn.; Eileen A. Elliot, New Haven, Conn.; Richard A. Flavell, Killingworth, Conn.; Joseph Madri, North Branford, Conn.; Scott Rollins, Monroe, Conn.; Leonard Bell, Woodbridge, Conn.; Stephen Squinto, Irvington, N.Y.

[73] Assignees: Oklahoma Medical Research Foundation, Oklahoma City, Okla.; Yale University, New Haven, Conn.

[*] Notice: This patent is subject to a terminal disclaimer.

[21] Appl. No.: 08/483,433

[22] Filed: Jun. 7, 1995

Related U.S. Application Data

[60] Division of application No. 08/087,007, Jul. 1, 1993, Pat. No. 5,705,732, and a continuation-in-part of application No. 07/906,394, Jun. 29, 1992, abandoned, and application No. 07/729,926, Jul. 15, 1991, abandoned, which is a continuation-in-part of application No. 07/365,199, Jun. 12, 1989, Pat. No. 5,135,916.

[51] Int. Cl.[7] ............... C12N 15/85; A01K 67/00; A61K 48/00; A61F 2/06
[52] U.S. Cl. ................ 800/14; 800/25; 623/1; 623/11; 424/93.21; 435/325; 435/455; 435/465
[58] Field of Search ............... 435/240.2, 172.3, 435/325, 455, 466; 800/2, DIG. 1–4, 25; 424/184.1, 185.1, 93.1, 93.2, 93.21; 514/44; 604/239, 187, 184, 185, 246; 128/DIG. 26; 536/23.1, 23.5; 623/1, 11

[56] References Cited

U.S. PATENT DOCUMENTS

| | | | |
|---|---|---|---|
| 4,883,755 | 11/1989 | Carabasi et al. | 435/240.2 |
| 5,336,615 | 8/1994 | Bell et al. | 435/240.2 |
| 5,416,260 | 5/1995 | Koller et al. | 800/2 |

FOREIGN PATENT DOCUMENTS

| | | | |
|---|---|---|---|
| WO 91/01140 | 2/1991 | WIPO | 435/240.2 |
| WO 91/05855 | 5/1991 | WIPO | 435/240.2 |

OTHER PUBLICATIONS

Houdebine, L–M. Production of pharmaceutical proteins from transgenic animals. J. of Biotech., vol. 34, pp. 269–287, 1994.

Report and recommendations of the panel to assess the NIH investment in research on gene therapy, Dec. 7, 1995.

Hansbrough et al. Expression of a liver fatty acid binding protein/human decay–accelerating factor/HLA–B44 chimeric gene in transgenic mice. Am J Physiol, vol. 260, No. 6 part 1, pp. g929–g939, Jun. 1991.

Grusby et al. Depletion of CD4+ T cells in major histocompatibility complex class II–deficient mice. Science, vol. 253, pp. 1417–1420, Sep. 20, 1991.

Bix et al, Rejection of class I MHC–deficient haemopoietic cells by irradiated MHC–matched mice. Nature, vol. 349, pp. 329–331, Jan. 24, 1991.

Zijlstra et al, Germ–line transmission of a disrupted beta–2–microglobulin gene produced by homologous recombination in embryonic stem cells. Nature, vol. 342, pp. 435–438, Nov. 23, 1989.

*Primary Examiner*—Bruce R. Campbell
*Assistant Examiner*—Deborah J. R. Clark
*Attorney, Agent, or Firm*—Arnall Golden & Gregory, LLP

[57] ABSTRACT

Genetically engineered cells are provided which can serve as universal donor cells in such applications as reconstruction of vascular linings or the administration of therapeutic agents. The cells include a coding region which provides protection against complement-based lysis, i.e., hyperacute rejection. In addition, the cell's natural genome is changed so that functional proteins encoded by either the class II or both the class I and the class II major histocompatibility complex genes do not appear on the cell's surface. In this way, attack by T-cells is avoided. Optionally, the cells can include a self-destruction mechanism so that they can be removed from the host when no longer needed.

17 Claims, 8 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2124 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (vii) IMMEDIATE SOURCE:
      (A) LIBRARY: GenBank HUMCD46Q
      (B) CLONE: HUMCD46 cDNA (xi) SEQUENCE DESCRIPTION: SEQ ID NO:1:

```
GAATTCGGGG ATAACAGCGT CTTCCGCGCC GCGCATGGAG CCTCCCGGCC GCCGCGAGTG      60

TCCCTTTCCT TCCTGGCGCT TTCCTGGGTT GCTTCTGGCG GCCATGGTGT TGCTGCTGTA     120

CTCCTTCTCC GATGCCTGTG AGGAGCCACC AACATTTGAA GCTATGGAGC TCATTGGTAA     180

ACCAAAACCC TACTATGAGA TTGGTGAACG AGTAGATTAT AAGTGTAAAA AAGGATACTT     240

CTATATACCT CCTCTTGCCA CCCATACTAT TTGTGATCGG AATCATACAT GGCTACCTGT     300

CTCAGATGAC GCCTGTTATA GAGAAACATG TCCATATATA CGGGATCCTT TAAATGGCCA     360
```

```
AGCAGTCCCT GCAAATGGGA CTTACGAGTT TGGTTATCAG ATGCACTTTA TTTGTAATGA      420

GGGTTATTAC TTAATTGGTG AAGAAATTCT ATATTGTGAA CTTAAAGGAT CAGTAGCAAT      480

TTGGAGCGGT AAGCCCCCAA TATGTGAAAA GGTTTTGTGT ACACCACCTC CAAAAATAAA      540

AAATGGAAAA CACACCTTTA GTGAAGTAGA AGTATTTGAG TATCTTGATG CAGTAACTTA      600

TAGTTGTGAT CCTGCACCTG GACCAGATCC ATTTTCACTT ATTGGAGAGA GCACGATTTA      660

TTGTGGTGAC AATTCAGTGT GGAGTCGTGC TGCTCCAGAG TGTAAAGTGG TCAAATGTCG      720

ATTTCCAGTA GTCGAAAATG GAAAACAGAT ATCAGGATTT GGAAAAAAAT TTTACTACAA      780

AGCAACAGTT ATGTTTGAAT GCGATAAGGG TTTTTACCTC GATGGCAGCG ACACAATTGT      840

CTGTGACAGT AACAGTACTT GGGATCCCCC AGTTCCAAAG TGTCTTAAAG TGTCGACTTC      900

TTCCACTACA AAATCTCCAG CGTCCAGTGC CTCAGGTCCT AGGCCTACTT ACAAGCCTCC      960

AGTCTCAAAT TATCCAGGAT ATCCTAAACC TGAGGAAGGA ATACTTGACA GTTTGGATGT     1020

TTGGGTCATT GCTGTGATTG TTATTGCCAT AGTTGTTGGA GTTGCAGTAA TTTGTGTTGT     1080

CCCGTACAGA TATCTTCAAA GGAGGAAGAA GAAAGGCACA TACCTAACTG ATGAGACCCA     1140

CAGAGAAGTA AAATTTACTT CTCTCTGAGA AGGAGAGATG AGAGAAAGGT TTGCTTTTAT     1200

CATTAAAAGG AAAGCAGATG GTGGAGCTGA ATATGCCACT TACCGACTA AATCAACCAC     1260

TCCAGCAGAG CAGAGAGGCT GAATAGATTC CACAACCTGG TTTGCCAGTT CATCTTTTGA     1320

CTCTATTAAA ATCTTCAATA GTTGTTATTC TGTAGTTTCA CTCTCATGAG TGCAACTGTG     1380

GCTTAGCTAA TATTGCAATG TGGCTTGAAT GTAGGTAGCA TCCTTTGATG CTTCTTTGAA     1440

ACTTGTATGA ATTTGGGTAT GAACAGATTG CCTGCTTTCC CTTAAATAAC ACTTAGATTT     1500

ATTGGACCAG TCAGCACAGC ATGCCTGGTT GTATTAAAGC AGGGATATGC TGTATTTTAT     1560

AAAATTGGCA AAATTAGAGA AATATAGTTC ACAATGAAAT TATATTTTCT TTGTAAAGAA     1620

AGTGGCTTGA ATCTTTTTT GTTCAAAGAT TAATGCCAAC TCTTAAGATT ATTCTTTCAC     1680

CAACTATAGA ATGTATTTTA TATATCGTTC ATTGTAAAAA GCCCTTAAAA ATATGTGTAT     1740

ACTACTTTGG CTCTTGTGCA TAAAAACAAG AACACTGAAA ATTGGGAATA TGCACAAACT     1800

TGGCTTCTTT AACCAAGAAT ATTATTGGAA AATTCTCTAA AAGTAAAGGG TAAATTCTCT     1860

ATTTTTTGTA ATGTGTTCGG TGATTTCAGA AAGCTAGAAA GTGTATGTGT GGCATTTGTT     1920

TTCACTTTTT AAAACATCCC TAACTGATCG AATATATCAG TAATTTCAGA ATCAGATGCA     1980

TCCTTTCATA AGAAGTGAGA GGACTCTGAC AGCCATAACA GGAGTGCCAC TTCATGGTGC     2040

GAAGTGAACA CTGTAGTCTT GTTGTTTTCC CAAAGAGAAC TCCGTATGTT CTCTTAGGTT     2100

GAGTAACCCA CTCTGCCCGA ATTC                                           2124
```

(2) INFORMATION FOR SEQ ID NO:2:

(i) SEQUENCE CHARACTERISTICS:
        (A) LENGTH: 2847 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens -continued (vii) IMMEDIATE SOURCE:
    (A) LIBRARY: GenBank HUMDAF; HUMDAFC1
    (B) CLONE: Human DAF cDNA (ix) FEATURE:
    (A) NAME/KEY: misc_feature
    (B) LOCATION: 1..819
    (D) OTHER INFORMATION: /note= "HUMDAFC1 (Promotor and 5'
        end of Exon 1, genomic sequence)"

(xi) SEQUENCE DESCRIPTION: SEQ ID NO:2:

```
TTCTCTCTAC AGTCAGTCTG GAGTAATCCC AAAGTGGTGT CTTTCGTAAA TAAGGAGAAC      60
CCGGGTGAAG AAAATGACTC CCACCCGAAC AAGGCATGAA CAATGTTCAC TCCCTACTGT     120
GTTATTCAAC CTGTTTCCCC AGGTCTCTGT TTTCACATTA GAGAGTGTTC TAGGAGATGA     180
CGCCCTTCCT CCTTAGTTAT TTCCCCACCC TCGTGCTGGC CTTTGACAGA CCTCCCAGTA     240
GAGGGCCCAA GACGCGGGTA GAGCACCGCG TCTCAGCGCC TGAGTCTCAG CCCCCGAACT     300
CCACCGCACC TCGAGGTCCC CTTGGCACGA CTCAAGCGCG GGGATGCTCC GCTTAGACGA     360
ACTCACGTGC GGGCAGCAAG GCCTGCGATA CTTGAGCACC CCTCCCCCTC TCCCGTTTAC     420
ACCCCGTTTG TGTTTACGTA GCGAGGAGAT ATTTAGGTTT CTAGAAGGCA GGTCATCGCA     480
GGCCCCACCC AGCAGTGGAG AGAGTGAGTC CAGAGGGTGT TGCCAGGAGC TCCTCCTCCT     540
TCCCCTCCCC ACTCTCCCCG AGTCTAGGGC CCCGGGGTAT GACGCCGGAG CCCTCTGACC     600
GCACCTCTGA CCACAACAAA CCCCTACTCC ACCCGTCTTG TTTGTCCCAC CCTTGGTGAC     660
GCAGAGCCCC AGCCCAGACC CCGCCCAAAG CACTCATTTA ACTGGTATTG CGGAGCCACG     720
AGGCTTCTGA CTTACTGCAA CTCGCTCCGG CCGCTGGGCG TAGCTGCGAC TCGGCGGAGT     780
CCCGGCGGCG CGTCCTTGTT CTAACCCGGC GCGCCATGAC CGTCGCGCGG CCGAGCGTGC     840
CCGCGGCGCT GCCCCTCCTC GGGGAGCTGC CCCGGCTGCT GCTGCTGGTG CTGTTGTGCC     900
TGCCGGCCGT GTGGGGTGAC TGTGGCCTTC CCCCAGATGT ACCTAATGCC CAGCCAGCTT     960
TGGAAGGCCG TACAAGTTTT CCCGAGGATA CTGTAATAAC GTACAAATGT GAAGAAAGCT    1020
TTGTGAAAAT TCCTGGCGAG AAGGACTCAG TGACCTGCCT TAAGGGCATG CAATGGTCAG    1080
ATATTGAAGA GTTCTGCAAT CGTAGCTGCG AGGTGCCAAC AAGGCTAAAT TCTGCATCCC    1140
TCAAACAGCC TTATATCACT CAGAATTATT TTCCAGTCGG TACTGTTGTG GAATATGAGT    1200
GCCGTCCAGG TTACAGAAGA GAACCTTCTC TATCACCAAA ACTAACTTGC CTTCAGAATT    1260
TAAAATGGTC CACAGCAGTC GAATTTTGTA AAAAGAAATC ATGCCCTAAT CCGGGAGAAA    1320
TACGAAATGG TCAGATTGAT GTACCAGGTG GCATATTATT TGGTGCAACC ATCTCCTTCT    1380
CATGTAACAC AGGGTACAAA TTATTTGGCT CGACTTCTAG TTTTTGTCTT ATTTCAGGCA    1440
GCTCTGTCCA GTGGAGTGAC CCGTTGCCAG AGTGCAGAGA AATTTATTGT CCAGCACCAC    1500
CACAAATTGA CAATGGAATA ATTCAAGGGG AACGTGACCA TTATGGATAT AGACAGTCTG    1560
TAACGTATGC ATGTAATAAA GGATTCACCA TGATTGGAGA GCACTCTATT TATTGTACTG    1620
TGAATAATGA TGAAGGAGAG TGGAGTGGCC CACCACCTGA ATGCAGAGGA AAATCTCTAA    1680
CTTCCAAGGT CCCACCAACA GTTCAGAAAC CTACCACAGT AAATGTTCCA ACTACAGAAG    1740
TCTCACCAAC TTCTCAGAAA ACCACCACAA AAACCACCAC ACCAAATGCT CAAGCAACAC    1800
GGAGTACACC TGTTTCCAGG ACAACCAAGC ATTTTCATGA ACAACCCCA AATAAAGGAA     1860
GTGGAACCAC TTCAGGTACT ACCCGTCTTC TATCTGGGCA CACGTGTTTC ACGTTGACAG    1920
GTTTGCTTGG GACGCTAGTA ACCATGGGCT TGCTGACTTA GCCAAAGAAG AGTTAAGAAG    1980
AAAATACACA CAAGTATACA GACTGTTCCT AGTTTCTTAG ACTTATCTGC ATATTGGATA    2040
```

```
AAATAAATGC AATTGTGCTC TTCATTTAGG ATGCTTTCAT TGTCTTTAAG ATGTGTTAGG    2100

AATGTCAACA GAGCAAGGAG AAAAAAGGCA GTCCTGGAAT CACATTCTTA GCACACCTGC    2160

GCCTCTTGAA AATAGAACAA CTTGCAGAAT TGAGAGTGAT TCCTTTCCTA AAAGTGTAAG    2220

AAAGCATAGA GATTTGTTCG TATTAAGAAT GGGATCACGA GGAAAAGAGA AGGAAAGTGA    2280

TTTTTTTCCA CAAGATCTGA AATGATATTT CCACTTATAA AGGAAATAAA AAATGAAAAA    2340

CATTATTTGG ATATCAAAAG CAAATAAAAA CCCAATTCAG TCTCTTCTAA GCAAAATTGC    2400

TAAAGAGAGA TGACCACATT ATAAAGTAAT CTTTGGCTAA GGCATTTTCA TCTTTCCTTC    2460

GGTTGGCAAA ATATTTTAAA GGTAAAACAT GCTGGTGAAC CAGGGTGTTG ATGGTGATAA    2520

GGGAGGAATA TAGAATGAAA GACTGAATCT TCCTTTGTTG CACAAATAGA GTTTGGAAAA    2580

AGCCTGTGAA AGGTGTCTTC TTTGACTTAA TGTCTTTAAA AGTATCCAGA GATACTACAA    2640

TATTAACATA AGAAAAGATT ATATATTATT TCTGAATCGA GATGTCCATA GTCAAATTTG    2700

TAAATCTTAT TCTTTTGTAA TATTTATTTA TATTTATTTA TGACAGTGAA CATTCTGATT    2760

TTACATGTAA AACAAGAAAA GTTGAAGAAG ATATGTGAAG AAAAATGTAT TTTTCCTAAA    2820

TAGAAATAAA TGATCCCATT TTTTGGT                                        2847
```

(2) INFORMATION FOR SEQ ID NO:3:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (vii) IMMEDIATE SOURCE:
        (B) CLONE: CD59

(xi) SEQUENCE DESCRIPTION: SEQ ID NO:3:

```
Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Leu Val Thr Pro Phe Leu Ala
            85                  90                  95

Ala Ala Trp Ser Leu His Pro
        100
```

(2) INFORMATION FOR SEQ ID NO:4:

(i) SEQUENCE CHARACTERISTICS:

-continued

```
            (A) LENGTH: 315 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens (vii) IMMEDIATE SOURCE:
            (B) CLONE: CD59

(xi) SEQUENCE DESCRIPTION: SEQ ID NO:4:

CTGCAGTGCT ACAACTGTCC TAACCCAACT GCTGACTGCA AAACAGCCGT CAATTGTTCA        60

TCTGATTTTG ATGCGTGTCT CATTACCAAA GCTGGGTTAC AAGTGTATAA CAAGTGTTGG       120

AAGTTTGAGC ATTGCAATTT CAACGACGTC ACAACCCGCT TGAGGGAAAA TGAGCTAACG       180

TACTACTGCT GCAAGAAGGA CCTGTGTAAC TTTAACGAAC AGCTTGAAAA TGGTGGGACA       240

TCCTTATCAG AGAAAACAGT TCTTCTGCTG GTGACTCCAT TTCTGGCAGC AGCCTGGAGC       300

CTTCATCCCT AAGTC                                                       315

(2) INFORMATION FOR SEQ ID NO:5:

(i) SEQUENCE CHARACTERISTICS:
            (A) LENGTH: 7 amino acids
            (B) TYPE: amino acids
            (C) STRANDEDNESS: single
            (D) TOPOLOGY: linear (xi) SEQUENCE DESCRIPTION: SEQ ID NO:5:

Leu Ile Gly Arg Lys Lys Thr
1               5

(2) INFORMATION FOR SEQ ID NO:6:

(i) SEQUENCE CHARACTERISTICS:
            (A) LENGTH: 5 amino acids
            (B) TYPE: amino acids
            (C) STRANDEDNESS: single
            (D) TOPOLOGY: linear (xi) SEQUENCE DESCRIPTION: SEQ ID NO:6:

Tyr Ile Gly Ser Arg
1               5
```

UNIVERSAL DONOR CELLS

This is a divisional of U.S. Ser. No. 08/087,007, filed Jul. 1, 1993, now U.S. Pat. No. 5,705,732, and a continuation-in-part of U.S. Ser. No. 07/906,394, filed Jun. 29, 1992, abandoned, and U.S. Ser. No. 07/729,926, filed Jul. 15, 1991, abandoned, which is a continuation-in-part of U.S. Ser. No. 07/365,199, filed Jun. 12, 1989, U.S. Pat. No. 5,135,916.

The U.S. Government has rights in this invention by virtue of Grants Nos. GM40924, 5 K11 HC02351, RO1 HL 28373, and 9T32 DK07556, awarded by the Department of Health and Human Services.

BACKGROUND OF THE INVENTION

This invention relates to genetically engineered endothelial cells and, in particular, to endothelial cells which have been modified to resist lysis and activation by complement and evade the host's immune mechanisms for removing foreign cells, when inserted into a non-autologous host.

Endothelial cells are specialized cells which form the lining of the heart and the blood vessels. Because of their direct contact with the circulating blood, a number of proposals have been made to genetically engineer these cells and use them as "in vivo" drug delivery systems, for example, by Culliton, B. J. 1989. "Designing Cells to Deliver Drugs," *Science* 246:746–751; and Zwiebel et al., "High-Level Recombinant Gene Expression in Rabbit Endothelial Cells Transduced by Retroviral Vectors," *Science* 243:220–222 (transfer of a human adenosine deaminase gene and a rat growth hormone gene to aortic endothelial cells using a retroviral vector and demonstration of the secretion of rat growth hormone from such cells after seeding onto a synthetic vascular graft).

Natural endothelial cells play important roles in normal physiology. In particular, these cells constitute the interface between the blood and the vessel wall and the organs of the body. As such, endothelial cells secrete various natural products directly into the blood stream, maintain an anti-thrombotic surface on the inside of the vessel, restrict leukocytes from penetrating the vessel wall, regulate various of the biological properties of smooth muscle cells, and participate in the control of vessel wall tone. Therefore, loss of endothelial cells results in the loss of these normal physiological processes and ultimately leads to pathological conditions such as coronary artery disease, organ transplant rejection and vasculitis.

Accordingly, in addition to their use as a medium for the in vivo administration of therapeutics, there is a need to provide genetically engineered endothelial cells to replace natural endothelial cells which have been lost due to disease or surgery.

In the past, proposals and/or efforts to use endothelial cells for either administration of therapeutics or cell replacement have generally been limited to autologous cells, i.e., cells derived from the organism undergoing treatment. Alternatively, the patient must be immunosuppressed, which is costly and leaves the patient vulnerable to infection.

This approach has suffered from a number of problems. For example, it is difficult to harvest healthy endothelial cells from the individual to be treated in significant quantities. The procedures for doing so require removal of a section of vasculature and then scraping or otherwise dislodging the endothelial cells from the walls of the vessels. As a result, to be useful for cell replacement, a large number of autologous endothelial cells must be grown in culture. To be of practical use, especially in the case of cell replacement, this culturing must take place quickly. Unfortunately, the cell doubling time for endothelial cells is on the order of at least 24 to 48 hours, leading to time periods on the order of a week or more before sufficient quantities of endothelial cells are available for genetic engineering or cell replacement. In addition, under normal physiological conditions, the cell doubling time for natural endothelial cells in vivo is also prolonged, making naturally occurring cell replacement in vivo following endothelial cell loss or damage highly inefficient.

Although the use of autologous endothelial cells for cell replacement therapy appears to be a difficult task, the potential use of microvascular capillary endothelial cells for systemic delivery of a therapeutic protein may allow for the use of either autologous or immunoprotected allogeneic or xenogeneic capillary endothelial cells. Several investigators have proposed the use of implanted genetically modified fibroblasts or keratinocytes as delivery systems and, while plausible, the expressed protein must diffuse through interstitial tissues, and into the microcirculation in order to gain access to the vascular system. This diffusional barrier to the systemic circulation is a considerable impediment to achieving adequate plasma levels of the desired therapeutic protein. Endothelial cells offer several advantages over fibroblasts in that they secrete their protein products directly into the bloodstream. Further, fibroblasts via their excessive production of fibrotic scar tissue, can prove highly detrimental to the host.

When a foreign cell is transplanted into a host, the immune system of the host rapidly mobilizes to destroy the cell and thereby protect the host. The immune system attack on the foreign cell is referred to as transplant rejection. The organism's first line of defense is through either lytic destruction or the activation of procoagulant and prothrombotic properties of the donor endothelial cell that may result from activation of the host's complement system and is generally known as the "hyperacute rejection response" or simply the "hyperacute response."

Several studies have demonstrated that the hyperacute response to transplants of either xenogeneic (from different species) and allotypic (from different individuals of the same species) organs is mediated by antibody-dependent activation of the complement system at the surface of the donor endothelium, as discussed, for example, by Platt et al., 1990 "Transplantation of discordant xenografts: a review of progress" *Immunology Today* 11:450–456. That is, the complement system attacks the endothelial cells lining the vessels of the transplanted organ. In studies of in vivo animal model systems aimed at assessing hyperacute rejection, 15 minutes after revascularization, xenoreactive antibodies were found to be deposited on the surface of the donor endothelium (Pober et al., *Human Immunol.* 28, 258–262 (1990); Haisch et al., *Surgery* 108, 306–311 (1990); Vercellotti et al., *J. Immunol.* 146, 730–734 (1991)). This was followed by activation of the complement system. Following complement activation there was significant aggregation and adhesion of platelets to the endothelium as well as formation of microthrombi and the migration of neutrophils and granulocytes into the interstitium. Ultimately, endothelial cells were destroyed, resulting in tissue ischemia and necrosis.

In addition to the rejection problems with xenografts, ten percent of allogeneic solid donor organs in HLA-identical matches have been found to be rejected by antibody/complement-mediated mechanisms (Brasile et al., *Trans. Proceed.* 19, 894–895 (1987)). In 78% of the cases of rejection under these conditions, the antibodies are directed against the vascular endothelial cells (Brasile et al., *Trans.* 40, 672–675 (1985)).

The results of these xenograft and allograft transplantations demonstrate that complement activation on the surface of the endothelial cell plays an important and early role in the process of graft rejection.

The complement system is a complex interaction of plasma proteins and membrane cofactors which act in a multistep, multi-protein cascade sequence in conjunction with other immunological systems of the host organism. The classic complement pathway involves an initial antibody recognition of, and binding to, an antigenic site on a target cell. This surface bound antibody subsequently reacts with the first component of complement, Clq, forming a Cl-antibody complex with Ca2+, Clr, and Cls which is proteolytically active. Cls cleaves C2 and C4 into active components, C2a and C4a. The C4b,2a complex is an active protease called C3 convertase, and acts to cleave C3 into C3a and C3b. C3b forms a complex with C4b,2a to produce C4b,2a,3b, which cleaves C5 into C5a and C5b. C5b forms a complex with C6 and this complex interacts with C7 in the fluid phase thereby exposing hydrophobic domains within C5b and C6 that stabilize the C5b,6,7 ternary complex in the cell membrane. C8, which is in the fluid phase, then binds to the C5b, 6, 7 ternary complex and this complex may contribute to the development of functional membrane lesions and slow cell lysis. Upon binding of C9 to C8 in the C5b-8 membrane complex, lysis of foreign cells is rapidly accelerated.

Control of the complement system is necessary in order to prevent destruction of autologous cells. One of the central molecules in the complement cascade is C3b which aggregates in increasing amounts on foreign substances or organisms thereby targeting them for removal. The complement precursor proteins are activated to form C3b in either of two ways: (i) by interacting with antibody bound to a foreign target (classical pathway) or (ii) non-specifically by progressive and rapidly increasing accumulation on foreign substances on the surface of foreign cells (the alternative pathway).

Activation of the alternative pathway relies on molecular structures on the target cell to upset the delicate balance of the proteins involved so that their activation and deposition are focused on the surface of the target cell. In the alternative pathway C3b is continuously activated at a slow rate in the fluid phase by various agents including endotoxin, lipopolysaccharide, and serum proteases that convert C3 to C3b. C5b can also be formed from C5 by plasmin, elastase and other serum proteases to initiate formation of the MAC.

In order to control this process of complement activation and to protect normal syngeneic cells from indiscriminate destruction, a family of cell-surface proteins has evolved that interacts with C3b molecules. These proteins are as follows:

(a) Membrane cofactor protein (MCP or CD46) which exists on all cells, except red blood cells, and binds to C3b and activates molecules that cleave C3b into inactive fragments before it can accumulate on the surface of a target cell to destroy that cell.

(b) Decay accelerating factor (DAF or CD55) which exists on all cells including red blood cells and prevents C3b from reacting with other complement components preventing destruction of the cell. CD55, unlike CD46, does not destroy C3b.

(c) Complement receptor 1 (CR1 or CD35) which exists on a select group of lymphocytes as well as erythrocytes, neutrophils, and eosinophils and causes degradation of C3b molecules adhering to neighboring cells.

(d) Factor H and C4b-binding protein which both inhibit C3 convertase activity of the alternative complement pathway.

All of these proteins are encoded at a single chromosomal location (chromosome 1, band 1q32) identified as the RCA, i.e., the regulators of complement activation. They are each uniquely characterized structurally by a short consensus repeating unit (SCR) of approximately 60 amino acids composed mostly of cysteine, proline, glycine, tryptophan, and several hydrophobic residues. Reid, et al., *Immunol. Today* 7, 230 (1986); Coyne, et al., *J. Immunol.* 149, 2906–2913 (1992). For CD46 and CD55, these SCRs are known to encode the functional domains of the proteins necessary for full complement regulatory activity. Adams, et al., *J. Immunol.* 147, 3005–3011 (1991). For a discussion of SCRs generally see Perkins et al., *Biochem.* 27, 4004–4012 (1988); for a discussion of SCRs of factor H and CD35 see Krych et al., *Proc. Natl. Acad. Sci. USA* 88, 4353–4357 (1991) and Weisman et al., *Science* 249, 146 (1990).

In addition to membrane and soluble inhibitors of the C3 convertase enzymes, human blood cells and the vascular endothelium express a cell surface glycoprotein, CD59, that serves to prevent assembly of the C5b-9 lytic MAC and, therefore, protects these cells from complement-mediated cell activation and lysis. U.S. Pat. No. 5,135,916 issued Aug. 4, 1992, assigned to the Oklahoma Medical Research Foundation, and U.S. Ser. No. 07/729,926 filed Jul. 15, 1991, assigned to the Oklahoma Medical Research Foundation and Yale University, disclose that the human complement regulatory protein CD59 can be used to protect non-human endothelial cells, for example, porcine endothelial cells, from attack by human complement, either when provided in solution with the cells or expressed in genetically engineered cells. See also Zhao et al., 1991 "Amplified gene expression in CD59-transfected Chinese Hamster Ovary cells confers protection against the membrane attack complex of human complement" *J. Biol. Chem.* 266:13418–13422. The homologous complement inhibitory activity of CD59 resides in its species-specific interaction with the terminal complement components C8 and C9, as further reported by Rollins and Sims, 1990. "The complement inhibitory activity of CD59 resides in its capacity to block incorporation of C9 into membrane C5b-9" *J. Immunol.* 144:3478–3483.

Although the use of CD59 does successfully address the problem of hyperacute rejection as a result of complement attack, it does not protect the cell against the overall immune attack of the host organism against foreign endothelial cells.

In stimulating immune responses, antigens elicit many molecular and cellular changes. Lymphocytes recognize antigens as foreign and are responsible for initiating both cellular and humoral responses against the presenting antigen. B lymphocyte cells respond to antigen by the production of antibodies against the presenting antigen; T lymphocytes respond by initiating a cellular response to the presenting antigen. The two major subsets of T cells are $T_H$ cells, involved in processing of antigen for presentation to B cells, characterized by the presence of a cell-surface glycoprotein called CD4, and cytolytic T lymphocytes (CTLs), involved in recognition of antigen on cell surfaces and lysis of cells recognized as foreign, characterized by the presence of a cell-surface glycoprotein called CD8. T cells recognize peptide fragments in conjunction with one of the two main classes of cell-surface glycoproteins of the major histocompatibility complex (MHC): either class I (MHC-I) or class II (MHC-II) proteins. CD8+ T cells recognize antigens in conjunction with MHC-I, whereas CD4+ T cells recognize them in conjunction with MHC-II.

The MHC contain three major classes of genes. Class I genes encode the principal subunits of MHC-I glycoproteins, called human leukocyte antigens in humans, the principle ones being HLA-A, B, and C. These are present on virtually all cells and play a major role in rejection of allografts. They also form complexes with peptide fragments of viral antigens on virus-infected cells: recognition of the complexes by CD8+ CTLs results in destruction of virus infected cells. Recognition of the complexes is by a single receptor on the T cells which recognizes antigen in combination with MHC.

Class II genes, the major classes in humans being known as DP, DQ (subclasses $\beta 2$, $\alpha 2$, and $\beta 1\alpha 1$) and DR (subclasses $\beta 1$, $\beta 2$, $\beta 3$ and $\alpha 1$), encode cell-surface glycoproteins that are expressed by antigen-presenting cells, principally B cells, macrophages and dendritic cells. Together with peptide fragments of antigens, the class II proteins form the epitopes that are recognized by T helper cells (CD4+). Class III genes encode at least three proteins of the complement cascade and two cytotoxic proteins, tissue necrosis factor and lymphotoxin, which are involved in diverse immune reactions that destroy cells.

T-cell mediated immune reactions can be organized into three sequential activation steps. First, CD4+ and CD8+ Tlymphocytes (T-cells) recognize the presence of non-autologous MHC class II and class I proteins, respectively, on the surface of the foreign cell.

Second, the T-cells are activated by interaction of a ligand with the T cell receptors and other accessory stimulatory molecules, so that activation depends upon a variety of variables including humoral signals such as cytokines received by protein receptors on the surface of the cells. Most important is the interaction between the antigen specific T cell receptor and ligand, a complex of MHC and antigenic peptide on the antigen presenting cell (APC). Other receptors present on the T cell must also be contacted by their ligands on APC to insure activation. Once activated, the T-cells synthesize and secrete interleukin-2 (IL-2) and other cytokines.

The cytokines secreted by the activated T-cells lead to the third, or effector, phase of the immune response which involves recruitment and activation of lymphocytes, monocytes, and other leukocytes which together lead to cell lysis, as reviewed, for example, by Pober et al., 1990 "The potential roles of vascular endothelium in immune reactions" *Human Immunol.* 28:258–262.

Historically, attempts to interrupt the T-cell immune response have generally met with limited success. For example, several strategies have tried to use reagents of various types, including antibodies and blocking proteins, to interfere with adhesion between T-cells and foreign cells. Lider et al., 1988 "Anti-idiotypic network induced by T cell vaccination against experimental autoimmune encephalomyelitis" *Science* 239:181 reported on the use of T-cell vaccines; Owhashiand et al., 1988 "Protection from experimental allergic encephalomyelitis conferred by a monoclonal antibody directed against a shared idiotype on rat T cell receptors specific for myelin basic protein" *J. Exp. Med.* 168:2153, reported on the use of T-cell receptor blocking antibodies; Brostoffand et al. 1984 "Experimental allergic encephalomyelitis: successful treatment in vivo with a monoclonal antibody that recognizes T helper cells" *J. Immunol.* 133:1938 reported on the use of antibodies to CD4; and Adorini et al., 1988 "Dissociation of phosphoinositide hydrolysis and Ca2+ fluxes from the biological responses of a T-cell hybridoma" *Nature* 334:623–628, reported on the use of blocking peptides that occupy T-cell receptors. These strategies have generally resulted in immune responses to the reagents, rather than the desired interruption of T-cell binding.

It would clearly be advantageous if one could decrease the probability of T-cell mediated reaction against transplanted cells, as well as complement-mediated attack and lysis of the cell.

It is therefore an object of the present invention to provide an improved method and compositions for constructing endothelial cells that are resistant to both complement and cellular attack when transplanted into a foreign host.

It is a further object of the present invention to provide genetically engineered cells that are not recognized as foreign when implanted into a foreign host and therefore evade attack by the immune system.

It is still further object of this invention to provide genetically engineered cells which after transplantation can resist complement-mediated attack and evade lymphocyte-mediated lysis, specifically CD4+ T-lymphocytes, and preferably CD8+ T-lymphocytes.

It is another object of the invention to provide a mechanism for selectively killing such genetically engineered cells when their presence in the host is no longer desired.

It is still another object of the present invention to provide a biological vehicle for delivery of therapeutic products.

SUMMARY OF THE INVENTION

Genetically engineered cells are provided which include a DNA sequence which is expressed by the cell and which codes for a protein having complement inhibitory activity that is not normally expressed in the cell. These cells may also be engineered so that they do not express on their cell surfaces functional proteins encoded by the class II major histocompatibility complex (MHC) genes, the HLA DP, DQ, and DR genes in human cells, or their equivalent in cells of a different species. Alternatively, the genetically engineered cells do not express on their cell surfaces the proteins encoded by the class I MHC genes, the HLA A, B and C genes in human cells, or their equivalent in cells of a different species, or they do not express either the class I and class II MHC genes. In some embodiments, the cells include a genetic (DNA) sequence which is expressed by the cell and which codes for a protein which in the presence of a selected agent results in death of the cell.

The genetic sequence which codes for a protein which has complement regulatory activity protects the cell from hyperacute rejection through attack and lysis resulting from activation of the complement system. The removal of the cell surface proteins encoded by the class I (for example, HLA A, B and C) and class II (for example, HLA DP, DQ, and DR) MHC genes makes the cells substantially unrecognizable by the host's CD8+ and CD4+ T-lymphocytes, respectively. The genetic sequence which codes for a protein which can produce cell death provides a mechanism for eliminating the genetically engineered cells from the host when their presence is no longer desired.

The cells are modified in culture using standard in vitro transfection techniques, or can be derived from transgenic animals modified as embryos. These modified cells can serve as universal donor cells for administering therapeutic agents to the host or as replacements for natural cells which have been damaged or lost. In the most preferred embodiment, the cells are dissociated endothelial cells.

Examples demonstrate expression of human CD59 in porcine endothelial cells protects the cells from hyperacute rejection by human complement, preventing both complement-mediated lysis and activation of the porcine endothelial cells; stable expression of hCD59 in mouse cells which protects the cells from complement mediated lysis, generation of transgenic mice with a high degree of endothelial cell expression of hCD59 in both systemic and pulmonary circulations, and in capillary, arteriolar, and arterial vasculatures; generation of recombinant mice bearing a deletion of the invariant chain (Ii) having reduced cell surface MHC class II expression and diminished ability to present exogenous protein antigen; rat capillary endothelial cells engineered to stably express human Apolipoprotein E in three dimensional cultures; and implantation into a rat of the engineered rat capillary endothelial cell network with vascular astomosis to the recipient.

DETAILED DESCRIPTION OF THE INVENTION

Figure 1:
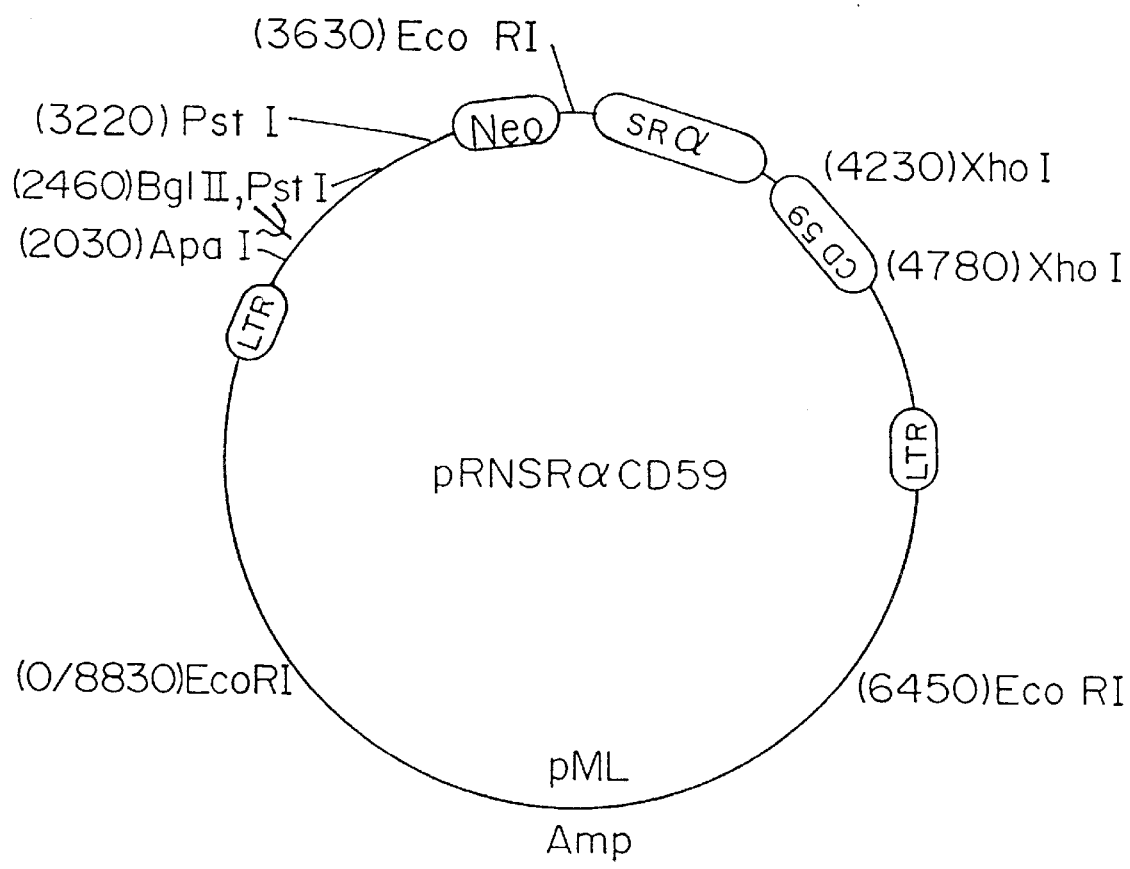
FIG. 1 shows the structure of the retroviral vector used in Example 1. This vector was constructed from a defective Moloney murine leukemia virus. The SV40 promoter was excised and replaced with the SRalpha promoter. A 500 bp cDNA fragment containing the CD59 coding sequence was cloned into an XhoI site and verified by restriction analysis. The resulting plasmid was designated pRNSRαCD59. Ecotropic retrovirus was produced by transfecting Psi-2 cells with polybrene and selecting in the toxic amino-glycoside G418. Amphotropic virus stocks were prepared by infecting the amphotropic packaging cell line Psi-AM with the ecotropic virus, were added directly to endothelial cell cultures in the presence of polybrene, and transfectants were selected with 400 μg/ml G418.

I. Cells to be Engineered and Hosts

Cells which have been genetically engineered can be transplanted into a host to allow them to both resist and evade the immune system of a host. The host will normally be a human or a domesticated farm animal.

Although described with reference to endothelial cells, especially dissociated endothelial cells for implantation or injection into a host, the methods and compositions described herein are not limited to endothelial cells. Other cell types can be similarly modified for transplantation. Examples of other cell types include fibroblasts, epithelial cells, skeletal, cardiac and smooth muscle cells, hepatocytes, pancreatic islet cells, bone marrow cells, astrocytes, Schwann cells, and other cell types, dissociated or used as tissue (i.e., organs). As described herein, "endothelial cells" will be construed to encompass modification of these other cell types unless otherwise specified or described specifically in the examples.

Sources of Cells

The cells can come from a variety of sources. Preferably, the cells are of non-human origin because of the ready availability of such cells in large quantities and at low cost. For example, the cells can be of porcine or bovine origin.

Cells from primates, including humans, can be used if desired. Even if human cells are used, protection from hyperacute rejection will in general still be required since complement-mediated cell attack can also occur even following allotypic transplantation.

The genetically engineered cells are normally derived from a single clone or, for some applications, a group of individually selected clones. In this way, the characteristics of the final pharmaceutical preparation can be accurately controlled both in terms of the overall properties of the cells and their genetic make-up. Such control is of importance in evaluating the effectiveness of particular treatment protocols and in obtaining regulatory approval for such protocols.

The cells are genetically engineered so that they express a complement inhibitory protein or proteins on their cell surface. The cells can also be genetically engineered so that they express deficient and/or dysfunctional proteins encoded by the class II, class I, or preferably the class I and class II, MHC genes on their cell surface. Even when human cells are used, it is beneficial to engineer the cells as described herein since the cell population will generally include non-autologous cells when the cells are obtained from an individual other than the one being treated.

The endothelial cells are obtained from the lining of a portion of the vascular system, e.g., a blood vessel or capillary, and are grown and maintained in a tissue culture or other suitable biological medium.

For example, porcine large vessel endothelial cells are isolated from the thoracic aortae of male pigs.

1. The thoracic aortae is removed from the sacrificed animal using sterile techniques, cross-clamping the aortic arch and the aorta just above the renal arterial ostia using sterile clamps.

2. The organs/tissues are placed in sterile PBS buffer, containing 10× penicillin, streptomycin and fungizone. These are transported on ice.

3. After placing the aorta on a sterile field in a laminar flow clean bench, the peri-aortic fat and adventitial tissue are dissected away from the aortae. With an assistant holding the aorta down, using the clamps and a sterile scissors, the vessel is cut open longitudinally, exposing the endothelium. The endothelium is then rinsed with the sterile PBS/antibiotic-containing buffer.

4. Following this, the endothelium is scraped off with a sterile scapel blade and the harvested endothelium is transferred into a sterile 15 cc conical centrifuge tube by displacing the cells with a stream of sterile PBS buffer. The tubes are centrifuged at 1200 RPM and the supernatant aspirated.

5. 5.0 ml of sterile media (DMEM, 10% heat-inactivated fetal calf sera, penicillin (100 U/ml), streptomycin (100 U/ml), 5 mM Hepes, 5 mM pyruvate and 5 mM glutamine, are added to each tube and the cell pellets resuspended in the media by gently pipetting the solution up and down in a sterile five ml pipette.

6. 5.0 ml aliquot of cells (harvested from each aorta) are placed into a Corning T25 tissue culture flask and the cultures incubated in a 5% $CO_2$, 95% air humidified atmosphere at 37° C.

7. The cells are then passaged at confluency at a 1 to 3 split ratio using 0.02% trypsin (Worthington Biochemical Corp.) in a $Ca^{++}$ and $Mg^{++}$-free PBS containing 0.01% EDTA to dislodge the cells from the plate and dissociate the cells.

Culturing and Storage of Cells

After being genetically engineered in the manner described below, the cells are normally stored in liquid nitrogen tanks until needed for the treatment of a particular patient. The ability to prepare the donor cells in advance and store them until needed is an important advantage.

Cells are then seeded onto a matrix for implantation. For example, dissociated endothelial cells are prepared for seeding onto the interior of Gortex™ as follows.

1. Sterile Gortex™ material is placed into a sterile Falcon™ 15 cc conical disposable test tube. Coating solution consisting of 0.1 M sodium carbonate buffer, pH 9.3, and 100 µg/ml acid soluble type I collagen is added to the test tube. Following an overnight incubation at 4° C., the Gortex™ is rinsed with sterile PBS. Type I collagen is used as a coating because it provides maximal, rapid endothelial cell adhesion (75% adhesion in 30 min and 80% adhesion in one hour) and migration. See, Madri, et al., "The collagenous components of subendothelium: Correlation of structure and function" *Lab. Invest.* 43:303–315 (1980).

2. The Gortex™ tubing is then closed at one end and endothelial cells are introduced into the lumen of the Gortex™ tubing and the other end is closed.

3. The segment(s) of Gortex™ are then placed in a sterile tube and the tube filled with media and rotated in a 5% $CO_2$, 95% air humidified atmosphere at 37° C. for one hour.

4. Remove the Gortex™ segments from the tubes and wash them with sterile media.

5. The Gortex™ segments are transplanted into the vasculature of the host.

II. Protection From Hyperacute Rejection

The lysis and activation of cells by complement has been determined to typically require only the terminal complement components, in contrast to previous reports that it may be essential to interrupt complement activation at the C3 stage, as described, for example, in PCT application WO 91/05855.

Sequential addition of C6,7,8, and 9 to C5b leads to the formation of a membrane attack complex (MAC), a pore-like complex which, when inserted into the plasma membrane of the target cell, increases membrane permeability to calcium and other ions. Consequently, lysis of the plasma membrane ensues and the cell is either destroyed, or alternatively, there is a non-lytic alteration of specific cell functions affecting vascular hemostases. In the case of human endothelial cells exposed to human serum complement, membrane deposition of the C5b-9 complex initiates a variety of procoagulant and prothrombotic changes in the cell that are expected to accelerate blood clotting and thrombus formation, as described, for example, by Hattori, et al., 1989 "Complement proteins C5b-9 induce secretion of high molecular weight multimers of endothelial von Willebrand Factor and translocation of granule membrane protein GMP-140 to the cell surface" *J. Biol. Chem.* 264:9053–9060; Hamilton, et al., 1990 "Regulatory control of the terminal complement proteins at the surface of human endothelial cells: Neutralization of a C5b-9 inhibitor by antibody to CD59" *Blood* 76:2572–2577; and Hamilton and Sims 1991 "The terminal complement proteins C5b-9 augment binding of high density lipoprotein and its apoproteins A-I and A-II to human endothelial cells" *J. Clin. Invest.* 88:1833–1840. These responses appear to depend upon insertion of C9 into the plasma membrane of the target cell and therefore can be prevented by interfering with assembly of the C5b-9 complex.

Membrane proteins inhibiting complement.

Specific membrane proteins which exhibit potent inhibitory activity for the complement cascade have been isolated and molecularly cloned.

In particular, with regard to the human complement system, protection against the pore-forming activity of the C5b-9 complex can be conferred on non-primate cells by transfection of such cells with a cDNA encoding the human complement regulatory protein CD59. This protein operates by limiting the incorporation of C9 into the membrane complex C5b-9, as reported by Zhao, et al., 1991 "Amplified gene expression in CD59-transfected Chinese Hamster Ovary cells confers protection against the membrane attack complex of human complement" *J. Biol. Chem.* 266:13418–13422; Rollins and Sims, 1990 "The complement inhibitory activity of CD59 resides in its capacity to block incorporation of C9 into membrane C5b-9" *J. Immunol.* 144:3478–3483 and Rollins, et al., "Inhibition of homologous complement by CD59 is mediated by a species-selective recognition conferred through binding to C8 within C5b-8 or C9 within C5b-9" *J. Immunol.* 146:2345–2351, incorporated herein by reference.

Other complement inhibitors which have been identified and can be used alone or in combination with CD59 include:

(1) CD46, also known as membrane cofactor protein (MCP), as described by Purcell, et al., 1990 "The human cell surface glycoproteins HuLy-m5, membrane cofactor protein (MCP) of the complement system, and trophoblast leucocyte common (TLX) antigen, are CD46" *J. Immunol.* 70:155–161; and Seya and Atkinson, 1989 "Functional properties of membrane cofactor protein of complement" *Biochem. J.* 264:581–588. This inhibitor functions by binding to complement component C3b thereby activating molecules that cleave C3b into inactive fragments preventing accumulation of C3b and, therefore, its contribution to the formation of the MAC. See also White et al. 1991 "Protection of mammalian cells from human complement-mediated lysis by transfection of human membrane cofactor protein (MCP) or decay accelerating factor (DAF)" *Int. Meeting on Xenotransplantation—: - - - (recombinant human CD46 shown to provide protection of non-primate cells from lysis by human complement).

(2) CD55, also known as decay accelerating factor (DAF), described by Nicholson-Weller et al., 1982 "Isolation of a human erythrocyte membrane glycoprotein with decay-accelerating activity for C3 convertases of the complement system" *J. Immunol.* 129:184; Lublin and Atkinson, 1989 "Decay accelerating factor: Biochemistry, molecular biology, and function" *Annu. Rev. Immunol.* 7:35; Lublin et al., 1987 "The gene encoding decay-accelerating factor (DAF) is located in the complement-regulatory locus on the long arm of chromosome 1" *J. Exp. Med.* 165:1731; and Medof et al., 1987 "Cloning and characterization of cDNAs encoding the complete sequence of decay accelerating factor of human complement" *Proc. Natl. Acad. Sci. USA* 84:2007. This inhibitor is a membrane bound protein of approximately 70 kD in molecular mass which interferes with the assembly of C3 convertase. See also White et al., 1991, reporting that recombinant DAF provides protection of non-primate cells from lysis by human complement.

The relative contributions of CD46, CD55, and CD59 in providing protection from complement-mediated lysis has been assessed in human amniotic epithelial cells (HAEC) by the use of specific blocking antibodies, as reported by Rooney et al., 1990 "Protection of human amniotic epithelial cells (HAEC) from complement-mediated lysis: expression on the cells of three complement inhibitory membrane proteins." *Immunology* 71:308–311. The results demonstrated that CD59 provide the most protection against complement attack, as compared with CD46 and CD55. Additionally, a patient with paroxysmal nocturnal hemoglobinuria, a rare disorder caused by an unusual susceptibility of erythrocytes to the lytic action of complement, was described as having an inherited deficiency of CD59 without a deficiency of CD55, by Yamashina et al. 1990 "Inherited complete deficiency of 20-kilodalton (CD59) as a cause of paroxysmal nocturnal hemoglobinuria" *New Engl. J. Med.* 323:1184–1189.

By contrast to the intravascular hemolysis observed for this patient reported to be deficient in CD59 but normal for decay accelerating factor (and presumably normal for other complement inhibitors), individuals with inherited defects or deficiencies in erythrocyte CD55 (Decay Accelerating Factor) generally do not exhibit intravascular hemolysis, as reported by Daniels, G. 1989 "Cromer-related antigens-blood group determinants on decay accelerating factor. *Vox. Sang.* 56:205; Holguin, et al. 1992 "Analysis of the effects of activation of the alternative pathway of complement on erythrocytes with an isolated deficiency of decay accelerating factor. *J. Immunol.* 148:498–502, suggesting the CD59 is necessary and sufficient to protect these cells from the cytolytic effects of complement in human plasma.

Cells suitable for transplantation into a foreign host are protected from complement-mediated lysis by introducing into the cell DNA encoding a protein, or combination of proteins, inhibiting complement-mediated lysis, for example, CD59, CD55, CD46 and/or other inhibitors of C8 or C9. CD59 is the preferred inhibitor, introduced into the cells by transfection or infection with a vector encoding the CD59 protein, and expressed on the surface of the transfected/infected cells. The inhibitor is preferably of the same species of origin as the host into which the cells are to be transplanted.

The gene encoding the complement inhibitor can be introduced into a cell of a different species of origin, for example, a human CD59 gene can be introduced into a porcine cell so that the cell resists attack when transplanted into a human, or the gene can be introduced into a cell of the same species of origin so that increased amounts of the protein are expressed on the surface of the cell. For example, the gene can be placed under the control of a promoter enhancing expression of the gene which is then inserted by homologous recombination into the host cell chromosome at the site where the gene is normally located, but under the control of the promoter which enhances expression, or can be inserted into the chromosome at another locus on the chromosome.

DNA sequence information for CD46, CD55 and CD59 has been reported in the literature.

The sequence reported by Lublin et al., 1988 "Molecular cloning and chromosomal localization of human membrane cofactor protein (MCP): Evidence for inclusion in the multi-gene family of complement-regulatory proteins" *J. Exp. Med.* 168:181–194, for CD46 is shown below (Sequence I.D. No. 1).

HUMCD46 cDNA Sequence Aquired from GenBank: HUMCD46Q

```
GAATTCGGGGATAACAGCGTCTTCCGCGCCGCGCATGGAGCCTCCCGGCCGCCGCGA
GTGTCCCTTTCCTTCCTGGCGCTTTCCTGGGTTGCTTCTGGCGGCCATGGTGTTGCT
GCTGTACTCCTTCTCCGATGCCTGTGAGGAGCCACCAACATTTGAAGCTATGGAGCT
CATTGGTAAACCAAAACCCTACTATGAGATTGGTGAACGAGTAGATTATAAGTGTAA
AAAAGGATACTTCTATATACCTCCTCTTGCCACCCATACTATTTGTGATCGGAATCA
TACATGGCTACCTGTCTCAGATGACGCCTGTTATAGAGAAACATGTCCATATATACG
GGATCCTTTAAATGGCCAAGCAGTCCCTGCAAATGGGACTTACGAGTTTGGTTATCA
GATGCACTTTATTTGTAATGAGGGTTATTACTTAATTGGTGAAGAAATTCTATATTG
TGAACTTAAAGGATCAGTAGCAATTTGGAGCGGTAAGCCCCCAATATGTGAAAAGGT
TTTGTGTACACCACCTCCAAAAATAAAAAATGGAAAACACACCTTTAGTGAAGTAGA
AGTATTTGAGTATCTTGATGCAGTAACTTATAGTTGTGATCCTGCACCTGGACCAGA
TCCATTTTCACTTATTGGAGAGAGCACGATTTATTGTGGTGACAATTCAGTGTGGAG
TCGTGCTGCTCCAGAGTGTAAAGTGGTCAAATGTCGATTTCCAGTAGTCGAAAATGG
AAAACAGATATCAGGATTTGGAAAAAAATTTTACTACAAAGCAACAGTTATGTTTGA
ATGCGATAAGGGTTTTTACCTCGATGGCAGCGACACAATTGTCTGTGACAGTAACAG
TACTTGGGATCCCCCAGTTCCAAAGTGTCTTAAAGTGTCGACTTCTTCCACTACAAA
ATCTCCAGCGTCCAGTGCCTCAGGTCCTAGGCCTACTTACAAGCCTCCAGTCTCAAA
TTATCCAGGATATCCTAAACCTGAGGAAGGAATACTTGACAGTTTGGATGTTTGGGT
CATTGCTGTGATTGTTATTGCCATAGTTGTTGGAGTTGCAGTAATTTGTGTTGTCCC
GTACAGATATCTTCAAAGGAGGAAGAAGAAAGGCACATACCTAACTGATGAGACCCA
CAGAGAAGTAAAATTTACTTCTCTCTGAGAAGGAGAGATGAGAGAAAGGTTTGCTTT
TATCATTAAAAGGAAAGCAGATGGTGGAGCTGAATATGCCACTTACCAGACTAAATC
AACCACTCCAGCAGAGCAGAGAGGCTGAATAGATTCCACAACCTGGTTTGCCAGTTC
ATCTTTTGACTCTATTAAAATCTTCAATAGTTGTTATTCTGTAGTTTCACTCTCATG
AGTGCAACTGTGGCTTAGCTAATATTGCAATGTGGCTTGAATGTAGGTAGCATCCTT
TGATGCTTCTTTGAAACTTGTATGAATTTGGGTATGAACAGATTGCCTGCTTTCCCT
TAAATAACACTTAGATTTATTGGACCAGTCAGCACAGCATGCCTGGTTGTATTAAAG
CAGGGATATGCTGTATTTTATAAAATTGGCAAAATTAGAGAAATATAGTTCACAATG
AAATTATATTTTCTTTGTAAAGAAAGTGGCTTGAAATCTTTTTTGTTCAAAGATTAA
TGCCAACTCTTAAGATTATTCTTTCACdAACTATAGAATGTATTTTATATATCGTTC
ATTGTAAAAAGCCCTTAAAAATATGTGTATACTACTTTGGCTCTTGTCATAAAAAC
AAGAACACTGAAAATTGGGAATATGCACAAACTTGGCTTCTTTAACCAAGAATATTA
TTGGAAAATTCTCTAAAAGTAAAGGGTAAATTCTCTATTTTTTGTAATGTGTTCGGT
GATTTCAGAAAGCTAGAAAGTGTATGTGTGGCATTTGTTTTCACTTTTTAAAACATC
CCTAACTGATCGAATATATCAGTAATTTCAGAATCAGATGCATCCTTTCATAAGAAG
TGAGAGGACTCTGACAGCCATAACAGGAGTGCCACTTCATGGTGCGAAGTAACACT
GTAGTCTTGTTGTTTTCCCAAAGAGAACTCCGTATGTTCTCTTAGGTTGAGTAACCC
ACTCTGCCCGAATTC
```

The sequence reported by Medof et al., 1987, for CD55 is shown below (Sequence I.D. No. 2).

Human DAF cDNA Sequence Aquired from GenBank HUMDAF; HUMDAFC1

TTCTCTCTACAGTCAGTCTGGAGTAATCCCAAAGTGGTGTCTTTCGTAAATAAGGAG
AACCCGGGTGAAGAAAATGACTCCCACCCGAACAAGGCATGAACAATGTTCACTCCC
TACTGTGTTATTCAAC
CTGTTTCCCCAGGTCTCTGTTTTCACATTAGAGAGTGTTCTAGGAGATGACGCCCTT
CCTCCTTAGTTATTTCCCCACCCTCGTGCTGGCCTTTGACAGACCTCCCAGTAGAGG
GCCCAAGACGCGGGTAGAGCACCGCGTCTCAGCGCCTGAGTCTCAGCCCCCGAACTC
CACCGCACCTCGAGGTCCCCTTGGCACGACTCAAGCGCGGGGATGCTCCGCTTAGAC
GAACTCACGTGCGGGCAGCAAGGCCTGCGATACTTGAGCACCCCTCCCCCTCTCCCG
TTTACACCCCGTTTGTGTTTACGTAGCGAGGAGATATTTAGGTTTCTAGAAGGCAGG
TCATCGCAGGCCCCACCCAGCAGTGGAGAGAGTGAGTCCAGAGGGTGTTGCCAGGAG
CTCCTCCTCCTTCCCCTCCCCACTCTCCCCGAGTCTAGGGCCCCGGGGTATGACGCC
GGAGCCCTCTGACCGCACCTCTGACCACAACAAACCCCTACTCCACCCGTCTTGTTT
GTCCCACCCTTGGTGACGCAGAGCCCCAGCCCAGACCCCGCCCAAAGCACTCATTTA
ACTGGTATTGCGGAG
CCACGAGGCTTCTGACTTACTGCAACTCGCTCCGGCCGCTGGGCGTAGCTGCGACTC
GGCGGAGTCCCGGCGGCGCGTCCTTGTTCTAACCCGGCGCGCCATGACCGTCGCGCG
CCGAGCGTGCCCGCGGCGCTGCCCCTCCTCGGGGAGCTGCCCCGGCTGCTGCTGCTG
GTGCTGTTGTGCCTGCCGGCCGTGTGGGGTGACTGTGGCCTTCCCCCAGATGTACCT
AATGCCCAGCCAGCTTTGGAAGGCCGTACAAGTTTTCCCGAGGATACTGTAATAACG
TACAAATGTGAAGAAAGCTTTGTGAAAATTCCTGGCGAGAAGGACTCAGTGACCTGC
CTTAAGGGCATGCAATGGTCAGATATTGAAGAGTTCTGCAATCGTAGCTGCGAGGTG
CCAACAAGGCTAAATTCTGCATCCCTCAAACAGCCTTATATCACTCAGAATTATTTT
CCAGTCGGTACTGTTGTGGAATATGAGTGCCGTCCAGGTTACAGAAGAGAACCTTCT
CTATCACCAAAACTAACTTGCCTTCAGAATTTAAAATGGTCCACAGCAGTCGAATTT
TGTAAAAAGAAATCATGCCCTAATCCGGGAGAAATACGAAATGGTCAGATTGATGTA
CCAGGTGGCATATTATTTGGTGCAACCATCTCCTTCTCATGTAACACAGGGTACAAA
TTATTTGGCTCGACTTCTAGTTTTTGTCTTATTTCAGGCAGCTCTGTCCAGTGGAGT
GACCCGTTGCCAGAGTGCAGAGAAATTTATTGTCCAGCACCACCACAAATTGACAAT
GGAATAATTCAAGGGGAACGTGACCATTATGGATATAGACAGTCTGTAACGTATGCA
TGTAATAAAGGATTCACCATGATTGGAGAGCACTCTATTTATTGTACTGTGAATAAT
GATGAAGGAGAGTGGAGTGGCCCACCACCTGAATGCAGAGGAAAATCTCTAACTTCC
AAGGTCCCACCAACAGTTCAGAAACCTACCACAGTAAATGTTCCAACTACAGAAGTC
TCACCAACTTCTCAGAAAACCACCACAAAAACCACCACACCCAAATGCTCAAGCAACA
CGGAGTACACCTGTTTCCAGGACAACCAAGCATTTTCATGAAACAACCCCAAATAAA
GGAAGTGGAACCACTTCAGGTACTACCCGTCTTCTATCTGGGCACACGTGTTTCACG
TTGACAGGTTTGCTTGGGACGCTAGTAACCATGGGCTTGCTGACTTAGCCAAAGAAG
AGTTAAGAAGAAAATACACACAAGTATACAGACTGTTCCTAGTTTCTTAGACTTATC
TGCATATTGGATAAAATAAATGCAATTGTGCTCTTCATTTAGGATGCTTTCATTGTC
TTTAAGATGTGTTAGGAATGTCAACAGAGCAAGGAGAAAAAAGGCAGTCCTGGAATC
ACATTCTTAGCACACCTGCGCCTCTTGAAAATAGAACAACTTGCAGAATTGAGAGTG

-continued
```
ATTCCTTTCCTAAAAGTGTAAGAAAGCATAGAGATTTGTTCGTATTAAGAATGGGAT

CACGAGGAAAAGAGAAGGAAAGTGATTTTTTTCCACAAGATCTGAAATGATATTTCC

ACTTATAAAGGAAATAAAAAATGAAAAACATTATTTGGATATCAAAAGCAAATAAAA

ACCCAATTCAGTCTCTTCTAAGCAAAATTGCTAAAGAGAGATGACCACATTATAAAG

TAATCTTTGGCTAAGGCATTTTCATCTTTCCTTCGGTTGGCAAAATATTTTAAAGGT

AAAACATGCTGGTGAACCAGGGTGTTGATGGTGATAAGGGAGGAATATAGAATGAAA

GACTGAATCTTCCTTTGTTGCACAAATAGAGTTTGGAAAAAGCCTGTGAAAGGTGTC

TTCTTTGACTTAATGTCTTTAAAAGTATCCAGAGATACTACAATATTAACATAAGAA

AAGATTATATATTATTTCTGAATCGAGATGTCCATAGTCAAATTTGTAAATCTTATT

CTTTTGTAATATTTATTTATATTTATTTATGACAGTGAACATTCTGATTTTACATGT

AAAACAAGAAAAGTTGAAGAAGATATGTGAAGAAAAATGTATTTTTCCTAAATAGAA

ATAAATGATCCCATTTTTTGGT
```

BOLD TEXT=HUMDAFC1 (Promoter and 5' end of Exon 1, genomic Sequence)
PLAIN TEXT=HUMDAF cDNA The amino acid and nucleic acid sequences reported by Philbrick, W. M., et al., 1990 *Eur. J. Immunol.* 20, 87–92, for CD59 are as follows (Sequence I.D. No. 3).

The amino acid sequence for the protein is:

```
L Q C Y N C P N P T A D C K T A V N C S S D F D A C L I T

K A G L Q V Y N K C W K F E H C N F N D V T T R L R E N E

L T Y Y C C K K D L C N F N E Q L E N G G T S L S E K T V

L L L V T P F L A A A W S L H P.
```

A cDNA sequence encoding the CD59 protein is (Sequence I.D. No. 4):

```
CTGCAGTGCTACAACTGTCCTAACCCAACTGCTGACTGCAAAACAGCCGTCAATTGT

TCATCTGATTTTGATGCGTGTCTCATTACCAAAGCTGGGTTACAAGTGTATAACAAG

TGTTGGAAGTTTGAGCATTGCAATTTCAACGACGTCACAACCCGCTTGAGGGAAAAT

GAGCTAACGTACTACTGCTGCAAGAAGGACCTGTGTAACTTTAACGAACAGCTTGAA

AATGGTGGGACATCCTTATCAGAGAAAACAGTTCTTCTGCTGGTGACTCCATTTCTG

GCAGCAGCCTGGAGCCTTCATCCCTAAGTC.
```

Matching oligonucleotide primers can be readily designed and then used to obtain full length cDNA sequences for these proteins by performing a polymerase chain reaction amplification on human Cdna. The oligonucleotide primers are preferably designed with specific restriction enzyme sites so that the full length Cdna sequences can be readily subcloned into vectors for use in transfecting/infecting the target donor cells.

A preferred transcription cassette for introduction and stable expression in endothelial cells of the sequences encoding the complement regulatory proteins is described in U.S. Ser. No. 08/021,602, abandoned, entitled "Transcriptional Casette for the Expression of Complement Regulatory Proteins in Transgenic Animals."

The transcriptional cassette for producing a transgenic non-human mammal having endothelial cells which express a heterologous complement regulatory protein includes: the human cytomegalovirus immediately-early gene 1 promoter and enhancer (CMV IE P/E), a cDNA coding sequence for said heterologous complement regulatory protein, said cDNA coding sequence being operatively linked to the CMV IE P/E, the Simian Virus 40 intron donor and acceptor splice sequence, and the Simian Virus 40 polyadenylation sequence.

Plasmid pUC19-hCD59, obtained from Yale University, New Haven, Conn., was used to construct this vector. Human CD59 cDNA was excised from the plasmid using the restriction enzymes BamHI and EcoRI. The human CD59 cDNA thus obtained was subcloned into the mammalian expression vector pcDNAI/Amp (Invitrogen, San Diego, Calif.) to yield pC8-hCD59-103. The pcDNAI/Amp mammalian expression vector contains the human cytomegalovirus (CMV) immediate-early gene (IE) promoter and enhancer, the SV40 consensus intron donor and acceptor splice sequences, and a consensus polyadenylation site.

Plasmid pC8-hCD59-103 has been deposited with the American Type Culture Collection, 12301 Parklawn Drive, Rockville, Md., 20852, United States of America, in *E. coli* straIN dh5α, and has been assigned accession number ATCC 69231. This deposit was made under the Budapest Treaty on the International Recognition of the Deposit of Microorganisms for the Purpose of Patent Procedure (1977).

In certain preferred embodiments, the cDNA coding sequence of the transcriptional cassette codes for CD59, CD55, and/or CD46, although the cassette can be used with other complement regulatory proteins now known or subsequently identified or developed. As used herein, the term "complement regulatory protein" means any protein which inhibits activation and/or lysis of cells by the complement system. This "cassette" can be used to make transgenic non-human mammals all of whose germ cells and somatic cells contain the transcriptional cassette, as well as vascularized organs and endothelial cells derived from such transgenic mammals. The vascularized organ may be any organ which expresses the complement regulatory protein(s) on its endothelial cells, but is preferably the heart, spleen, kidney, lung, pancreas, or liver, i.e., the organs for which substantial transplantation demand exists.

Introduction of DNA Encoding the Complement Inhibitors into the Endothelial Cells.

DNA encoding the complement inhibitors can be introduced into the cells in culture using transfection or into embryos for production of transgenic animals expressing the complement inhibitors on the surface of their cells.

Introduction into Cells in Culture.

As known in the art, transfection can be accomplished by electroporation, calcium phosphate precipitation, a lipofectin-based procedure, or microinjection or through use of a "gene gun". In each case, Cdna for the inhibitory protein, such as CD59, is subcloned into a plasmid-based vector which encodes elements for efficient expression in the genetically engineered cell. The plasmid-based vector preferably contains a marker such as the neomycin gene for selection of stable transfectants with the cytotoxic aminoglycoside G418 in eukaryotic cells and an ampicillin gene for plasmid selection in bacteria.

Infection, which for endothelial cells is preferred, is accomplished by incorporating the genetic sequence for the inhibitory protein into a retroviral vector. Various procedures are known in the art for such incorporation. One such procedure which has been widely used in the art employs a defective murine retrovirus, Psi-2 cells for packaging the retrovirus, and the amphotropic packaging cell line Psi-AM to prepare infectious amphotropic virus for use in infecting the target donor cells, as described by Kohn et al., 1987 "Retroviral-mediated gene transfer into mammalian cells" *Blood Cells* 13:285–298.

Alternatively, rather than a defective Moloney murine retrovirus, a retrovirus of the self-inactivating and double-copy type can be used, such as that described by Hantzopoulos et al., 1989 "Improved gene expression upon transfer of the adenosine deaminase minigene outside the transcriptional unit of a retroviral vector" *Proc. Natl. Acad. Sci. USA* 86:3519–3523.

Introduction into Embryos for Production of Transgenic Animals Expressing Complement Inhibitor on the Surface of their Cells A variety of methods are known to those skilled in the art for making transgenic animals expressing a complement inhibitory protein on the surface of the cells for use as a source of modified cells for transplantation. Examples of particularly useful animals include rabbits and pigs, although transgenic mice, rats, rabbits, pigs, sheep, and cattle have been made using standard techniques. The most well known method for making a transgenic animal is by superovulation of a donor female, surgical removal of the egg and injection of the genetic material in the pronuclei of the embryo, as taught by U.S. Pat. No. 4,873,191 to Wagner, the teachings of which are incorporated herein. Another commonly used technique involves the genetic manipulation of embryonic stem cells (ES cells), as specifically described below in Example 3.

ES cells are grown as described, for example, in Robertson, E. J. "Embryo-derived stem cell lines" in: Teratocarcinomas and embryonic stem cells: A practical approach. E. J. Robertson, ed. 71–112 (Oxford-Washington, D.C.: IRL Press, 1987). ES cells are maintained in a pluripotent state in culture media containing recombinant Leukemia Inhibitory Factor (LIF) as described in U.S. Pat. No. 5,166,065 to Williams et al. Genetic material is introduced into the embryonic stem cells, for example, by electroporation according to the method of McMahon, A. P., and Bradley, A. *Cell* 62, 1073–1085 (1991). Colonies are picked from day 6 to day 9 of selection into 96 or 24 well dishes (Costar) and expanded and used to isolate DNA for Southern blot analysis.

Chimeric mice are generated as described in Bradley, "Production and analysis of chimaeric mice" in *Teratocarcinomas and embryonic stem cells: A practical approach* E. J. Robertson, ed. pp. 113–151 (Oxford, Washington, D.C. IRL Press 1987), the teachings of which are incorporated herein. Genetic material is injected into blastocysts. From those implanted females that become pregnant, chimaeras are selected from the offspring and bred to produce germline chimaeras for use as donor animals.

III. Protection From T-Cells

In contrast to the previous efforts to block the T cell immune-mediated response using antibodies or blocking compounds, genetic engineering of the cells are used to interrupt the T-cell immune response. The donor endothelial cells are genetically engineered to not express on their surface class II MHC molecules. More preferably, the cells are engineered to not express substantially all cell surface class I and class II MHC molecules. As used herein, the term "not express" may mean either that an insufficient amount is expressed on the surface of the cell to elicit a response or that the protein that is expressed is deficient and therefore does not elicit a response.

As used herein, the MHC molecules are referred to as HLA molecules, specifically of classes HLA A, B and C, and class II HLA DP, DQ, and DR, and their subclasses. This terminology is generally construed as specific to the human MHC, but is intended herein to include the equivalent MHC genes from the donor cell species, for example, if the cells are of porcine origin, the term HLA would refer to the equivalent porcine MHC molecules, whether MHC I or II.

When the class II MHC molecules are removed, CD4+ T-cells do not recognize the genetically engineered endothelial cells; when both the class I and class II MHC molecules are removed neither CD4+ nor CD8+ cells recognize the modified cells.

The relative importance of the CD4+ and CD8+ T-cell subpopulations in mediating immune responses, in particular allograft rejection, has been approached experimentally. Both experiments of nature and gene targeting by homologous recombination have provided some insights. For example, the AIDS virus (HIV) selectively depletes CD4+ T-cells and not CD8+ T-cells and virtually destroys the body's immune defense. Additionally, although homologous recombination and disruption of the β2-microglobulin gene in mice results in elimination of CD8+ T-cells, the mice inheriting this genotype remain healthy and are capable of resisting infection by foreign organisms such as viruses, as reported by Zijlstra et al., 1989 "Germ-line transmission of a disrupted β2-microglobulin gene produced by homologous recombination in embryonic stem cells" *Nature* 342:435438; and Koller et al., 1990 "Normal development of mice deficient in β2M, MHC class I proteins, and CD8+ T cells" *Science* 248:1227–1230. These two observations together suggest that CD4+ T-cells play a central and essential role in immune responses in general, while CD8+ T-cells play a specialized and less essential role in host defense mechanisms.

The preferred genetic modification performed on the endothelial cells includes 1) disrupting the endogenous invariant chain gene which functions in the assembly and transport of class II MHC molecules to the cell surface and loading of antigenic peptide, and 2) disrupting the endogenous $\beta_2$-microglobulin gene ($\beta_2$M gene) which codes for a protein required for the cell surface expression of all class I MHC molecules. Alternatively, just the invariant chain gene is disrupted. Invariant chain is believed to be required for the insertion of antigienic peptide fragments into the MHC class II molecule. Together, the antigenic peptide and MHC is recognized by T cells. In the absence of antigenic peptide, T cell recognition is not normally obtained, nor is the MHC class II molecule folded properly. Thus, in cells lacking invariant chain, presentation of peptide will be abrogated and even if minuscule amounts of cell surface MHC are obtained, they may be devoid of peptide and therefore, non-immunogenic.

The disruption of these genes is accomplished by means of a homologous recombination gene targeting technique, as described by Zijlstra et al., 1989; Koller et al., 1990; and Example 3 below showing disruption of the invariant chain gene.

The technique is applied to suppress expression of the class I MHC proteins on the cell surface as follows. First, the complete $\beta_2$M gene for the target donor endothelial cell is cloned, e.g., for porcine endothelial cells the porcine β2M gene is cloned. This is done by first obtaining cDNA for a homologous $\beta_2$M gene, such as the mouse β2M gene. DNA sequence information for the mouse $\beta_2$M cDNA has been reported by Parnes et al., 1983 *Nature* 302:449–452. Matching oligonucleotide primers are readily designed to hybridize by complementary base pairing to the extreme 5' and 3' ends of the mouse $\beta_2$M cDNA. These oligonucleotide primers are then used to obtain full-length cDNA sequences for the mouse $\beta_2$M protein by performing a polymerase chain reaction amplification on mouse cDNA. The oligonucleotide primers are preferentially designed to encode specific restriction sites at their ends so that full-length cDNA sequences can be readily subcloned into plasmids.

The full-length mouse $\beta_2$M cDNA can then be used as a radiolabeled hybridization probe to screen cDNA libraries prepared from the source of the target donor endothelial cells, e.g., for porcine endothelial cells the mouse $\beta_2$M cDNA is used as a hybridization probe to screen a porcine cDNA library which has been cloned into a lambda phage vector. Positive hybridizing clones are selected, purified, subcloned into plasmid vectors and then sequenced using methods known in the art.

The complete porcine $\beta_2$M gene, including untranslated nucleotide residues as well as the portion of the gene which codes for the expressed protein, can then be cloned by screening a porcine genomic DNA library cloned into a lambda phage vector with radiolabeled porcine $\beta_2$M cDNA as a hybridization probe. Positive clones are selected, purified, subcloned into plasmid vectors and sequenced using methods known in the art.

Once cloned, the $\beta_2$M gene is subcloned into a plasmid based or preferentially a retroviral-based vector (the "gene targeting vector") such that the reading frame of the $\beta_2$M gene is disrupted by insertion of a short DNA sequence which allows for positive selection of recombination in the endothelial cells, for example, a neomycin resistance gene (hereinafter referred to as the "positive selection gene"). The gene targeting vector also carries an additional selection gene (the "negative selection gene"), outside of the disrupted $\beta_2$M gene region which allows for selection against non-homologous recombination, i.e., for selection against incorporation of the entire plasmid into the genetic information of the cell rather than just the portion of the plasmid carrying the disrupted $\beta_2$M gene. The negative selection gene can be, for example, a herpes simplex thymidine kinase gene.

The gene targeting vector is then transfected/infected into the cells as described above and homologous recombination events are selected by screening for clones which express the positive selection gene but not the negative selection gene.

The same procedures are used to achieve homologous recombination of the invariant chain gene as demonstrated in Example 3 below.

IV. Cell Termination

Since the engineered cells resist attack by the complement system and evade the T-cell system, the cells and their progeny in theory can exist essentially indefinitely within the host organism. Since occasions may arise when it is desirable to remove these cells from the host, further genetic engineering is preferably performed wherein the cells are provided with an internal "self-destruct" or "suicide" mechanism.

In general terms, such a mechanism involves including in the cell a gene which expresses a protein, usually an enzyme, which confers lethal sensitivity of the cell to a specific reagent not normally present in the cell's environment. For example, the bacterial enzyme cytosine deaminase (CyD) converts the non-toxic drug 5-fluorocytosine to 5-fluorouracil which in turn is converted within the cell to 5-fluorouridine 5'-triphosphate and 5-fluoro-2'-deoxyuridine 5'-monophosphate which inhibit both RNA and DNA synthesis and thereby result in cell death, as reported by Mullin, et al., 1992 "Transfer of the bacterial gene for cytosine deaminase to mammalian cells confers lethal sensitivity to 5-fluorocytosine: a negative selection system" *Proc. Natl. Acad. Sci. USA* 89:33–37.

Accordingly, by inserting the gene for bacterial CyD into the genome of the donor endothelial cell, cell death can be accomplished at any desired time by simply administering 5-fluorocytosine to the host organism. The sequence of the bacterial CyD gene is known and thus incorporation of the gene into the donor endothelial cells can be preformed in a manner similar to that used to insert the CD59 gene.

Other genes now known or subsequently identified, which confer lethal sensitivity to a selected material, can also be used for this purpose.

V. Clinical Applications

As discussed above, the engineered cells can be used for cell replacement and for drug administration.

Treatment of coronary artery disease.

For example, coronary artery disease is caused by a blockage inside blood vessels, reducing the delivery of oxygen and nutrients to the heart. The current treatment for coronary artery blockade is either to mechanically dilate the blocked vessel from the inside with an angioplasty balloon or to use a replacement vessel, e.g., a synthetic graft or a section of the saphenous vein, to bypass or form a new channel around the blockage.

Coronary angioplasty involves the insertion of a catheter from the leg vessel to the coronary artery and inflation of a balloon at the tip of the catheter to dilate the atherosclerotic plaque. This balloon inflation unfortunately has the undesired side effect of removing endothelial cells from the inner lining of the blood vessel.

In terms of clinical practice, reocclusion of the treated vessel following coronary angioplasty, i.e., restenosis, is a significant medical problem since it occurs within six months following 30–50% of the procedures performed and is associated with substantial patient morbidity and health care expenditures. The principal reasons for the restenosis are acute thrombus formation due to loss of the antithrombotic surface provided by the endothelial cells and neointima formation due to unchecked smooth muscle cell stimulation by blood-borne cells, again due to the loss of the protective endothelial cell layer.

Coronary bypass graft surgery does not involve removing the blockage to blood flow in the coronary artery, using instead a bypass to detour blood flow around the blocked vessel to supply the remainder of the heart muscle. When a portion of the saphenous vein is used to form the bypass, the inside lining of endothelial cells is normally stripped off the vessel wall, and the smooth muscle cells in the blood vessel wall injured.

The loss of the endothelial lining results in the loss of several critical endothelial properties including loss of the anticoagulant surface, loss of important smooth muscle cell regulatory force, and the loss of the protective vessel wall covering which shields smooth muscle cells from platelets, monocytes, and lymphocytes. The subsequent response of the blood vessel to this pathologic injury is two-fold: 1) the physiological and beneficial migration of endothelial cells from the edge of the wound to restore luminal integrity and 2) the pathophysiological migration of smooth muscle cells from the interior of the blood vessel wall toward the lumen resulting in the neointima formation and postintervention occlusion.

Occlusion of peripheral arterial and coronary artery bypass grafts is a frequent and important clinical finding. Two-thirds of the saphenous vein coronary bypass grafts are either severely diseased or entirely occluded by six to eleven years following bypass surgery. Peripheral arterial bypass grafts generally suffer occlusion within two to five years.

Synthetic grafts also exhibit high rates of occlusion. Initially, grafts of this type are not endothelialized. This results in a substantial incidence of early occlusion due to thrombosis. With time, the grafts become partially re-endothelialized by migration of arterial endothelial cells from the proximal and distal anastomotic sites or from ingrowth of capillary endothelial cells through the porous synthetic graft onto the luminal surface. However, the process of endothelial cell migration is normally slow and does not permit total coverage of the graft by arterial endothelial cells. Further, ingrowing capillary endothelial cells are less capable of inhibiting clot formation than arterial endothelial cells. Attempts to reseed peripheral grafts with autologous endothelial cells have demonstrated that incomplete coverage of the graft at the time of seeding results in graft closure and lack of clinical benefit of the seeding procedure.

The genetically engineered cells described herein provide an important mechanism for addressing these critical problems in revascularization. These cells can be used to re-endothelialize denuded vessels or grafts without significant rejection by the patient's immune system. Moreover, since the cells can be grown in large numbers before the surgical procedure, adequate supplies are available for coverage of large areas of denuded vessel or naked graft. In this connection, further genetic engineering of the endothelial cells can be performed in accordance with copending application U.S. Ser. No. 07/820,011, filed Jan. 6, 1992, entitled "Genetically Engineered Endothelial Cells Exhibiting Enhanced Migration and Plasminogen Activator Activity," the teachings of which are incorporated herein, so as to increase the rate of migration of the donor endothelial cells and thus achieve more rapid re-endothelialization.

Although not preferred embodiment, capillary endothelial cells can also be isolated from human sources, and can even be autologous. For example, cells can be isolated from subcutaneous fat via liposuction and cultured with known human endothelial cell growth factors.

A typical procedure for implanting universal donor endothelial cells in a patient's coronary artery is as follows:

1. Performing diagnostic catheterization of the patient to determine the severity, location and amenability of the coronary (or peripheral) artery disease to angioplasty, atherectomy, laser therapy, or other forms of mechanical revascularization.
2. Assuming step (1) determines that therapeutic angioplasty is appropriate, performing a standard balloon angioplasty procedure.
3. Removing the genetically engineered endothelial cells described herein from storage under liquid nitrogen, thawing the cells to 37° C. and preparing them for installation by way of the angioplasty procedure by suspending them in sterile buffered media.
4. Using a standard wire exchange technique, removing the balloon angioplasty catheter and replacing it with a double balloon catheter having an infusion exit port positioned between the two balloons.
5. Positioning the double balloon catheter tip in the angioplastied coronary artery with the double balloons straddling the denuded segment of the artery, i.e., the portion of the artery in which the endothelial lining has been removed by the angioplasty procedure.
6. Gently inflating the double balloons while supporting the distal coronary circulation with standard perfusion techniques.
7. Introducing the engineered endothelial cells into the extracorporeal end of the double balloon catheter and infusing the cells into the isolated space in the blood vessel between the two balloons at a concentration of, for example, $2-10 \times 10^6$ cells per 10 milliliters of solution, to seed the denuded portion of the vessel.
8. After approximately twenty to thirty minutes, deflating the double balloon catheter so as to restore normal antegrade coronary perfusion,
9. Removing the double balloon catheter followed by standard post catheterization procedures.

Similarly, a synthetic or autologous vascular graft or stent can be coated with genetically engineered endothelial cells and then implanted in a patient by:

1. Performing diagnostic catheterization of the patient to determine the severity, location and amenability of the coronary (or peripheral) artery disease to vascular bypass surgery with autologous, synthetic, or other graft material.

2. In the case of a synthetic graft or stent, such as a graft or stent made of DACRON or stainless steel, coating the graft or stent with Type I collagen and fibronectin in saturating amounts greater than or equal to 25 mg/ml in carbonate buffer, pH 9.4; or in the case of an autologous graft, harvesting the saphenous vein or other vessel using conventional surgical techniques.

3. Cannulating the proximal end and ligating the distal end of the synthetic or saphenous vein graft.

4. Removing the genetically engineered endothelial cells from storage under liquid nitrogen, thawing them to 37° C., and then preparing them for seeding of the graft by suspending them in sterile buffered media.

5. Injecting the engineered endothelial cells, at a concentration of, for example, $2–10\times10^6$ cells per 10 milliliters of solution, through the proximal cannulation port into the lumen of the graft and rotating the graft for approximately 60 minutes to allow the universal donor endothelial cells to cover the graft surface.

6. Implanting the seeded graft in the coronary or peripheral artery using standard fine surgical techniques.

In addition to their use for cell replacement, the genetically engineered endothelial cells provide an excellent mechanism for the administration of therapeutic agents either locally at the site of cell implantation or systemically. These cells might also secrete PDGF or FGF antagonists, thrombolytics, or thrombin antagonists, so as to inhibit restenosis in a vessel or graft wall. Systemic drug delivery via universal donor endothelial cells might be most effectively accomplished by the use of genetically engineered microvascular (capillary) endothelial cells which offer several advantages including a relatively large surface area to volume ratio, especially when the cells are seeded into a capillary network as described below, and direct secretion of therapeutic protein products without any barrier to diffusion. Examples of the types of agents which can be administered in this way include blood clotting factors, clot dissolving factors, hormones, growth factors, cytokines, enzymes, and cholesterol binding or removing proteins. In each case, an appropriate gene or combination of genes is inserted into the genome of the donor endothelial cells prior to transplantation.

For most clinical indications, seeding of genetically engineered endothelial cells in large vessels or vascular grafts will not allow production of proteins at therapeutic levels because of the limited number of cells that can be accommodated on a two-dimension surface. A solution to the limitations of the relatively low density of endothelial cells which are available when seeded on a two dimensional surface is to take advantage of the biological properties of microvascular capillary endothelial cells. For example, several groups have demonstrated in vitro formation of stable capillary networks when microvascular capillary endothelial cells are maintained in a three dimensional culture system consisting of extracellular matrix components such as collagen in the presence of angiogenic factors. Indeed there are broad phenotypic changes in microvascular endothelial cells cultured in three dimensions as compared to cells cultured in two dimensions. Importantly though, this culture system provides for the maintenance of large numbers of cells in a relatively small volume. However, for this endothelial cell culture system to be useful for systemic protein delivery in vivo, several important additional properties must be demonstrated. First, these cells must be amenable to genetic engineering and should continue to express their recombinant protein even when maintained in a three dimensional matrix of extracellular matrix components. Further, these three dimensional cultures must be transplantable into recipients and, preferably, demonstrate vascular anastomosis to the recipient circulation in vivo.

Although not a preferred embodiment, capillary endothelial cells can also be isolated from human sources, including autologous sources, as described by U.S. Pat. No. 4,820,626 to Williams and Jarrell Sources of human capillary endothelial cells include omental fat, subcutaneous fat, or perinephric fat. For example, cells can be isolated from subcutaneous fat via liposuction and cultured with known endothelial cell growth factors.

A typical procedure for isolating cells of this type, for example, from a porcine source, is as follows:

1. Porcine microvascular endothelial cells (PMEC) are isolated by first removing the epididymal fat pads and/or kidneys from male pigs using sterile techniques. To do this, the organs or tissues are placed in sterile HEPES buffer (pH 7.4) which contains 140 mM NaCl, 10 mM HEPES, 10 mm KCl, 0.1 mm $CaCl_2$, 0.2 mm $MgCl_2$, 11 g/liter $NaHCO_3$, 5.0 g/liter glucose, 100 U/ml penicillin, and 100 U/ml streptomycin. For kidneys, the peri-renal fat is dissected away and the kidneys are placed in sterile HEPES buffer as above.

2. The large visible vessels are dissected away from the epididymal fat and the fat is then placed into sterile HEPES buffer. The fatty tissue is placed into 50 ml sterile Falcon "Blue Max" tubes containing a small amount of sterile HEPES buffer and the fat is minced for 3 to 5 minutes with a scissors.

3. The minced tissue is then placed into 50 ml Erlenmeyer flasks containing equal volumes of sterile HEPES buffer containing 5 mg/ml of collagenase and 5 mg/ml of bovine serum albumin (BSA). The flasks are incubated at 37° C. with agitation for 20 minutes. A small aliquot (0.1 ml) is removed from each flask every 20 minutes and then examined for the appearance of tube-like fragments of the capillary bed. The incubation is continued until the majority of the minced tissue contains tube-like fragments and single cells.

4. The cell suspension is centrifuged at 200×g for 7 minutes in 15 ml sterile conical tubes. The top white fatty layer is then aspirated off and the pellets are resuspended in 10 ml of HEPES buffer containing 10% BSA and then recentrifuged and resuspended an additional two times.

5. The resultant pellets are resuspended in 45% Percoll and centrifuged at 15,000×g for 20 minutes at 4° C. in a SS34 fixed angle rotor. The tufts of the PMECs are in a milky off-white layer beneath the top-most adipocyte-containing layer and above a translucent layer containing larger vessel fragments. The microvascular tufts and free endothelial cells are collected with a sterile pipette and then pelleted by centrifugation in HEPES-BSA at 200×g for 3 minutes. The tufts are resuspended in media (Medium 199E containing 20% heat-inactivated FBS, Penicillin, streptomycin, 5 mM HEPES, 5 mM Pyruvate, and 5 mm glutamine mixed 1:1 with the same medium containing 10% FBS which has been conditioned for 48 hours by incubating over confluent endothelial cell cultures).

6. The cells are then seeded into tissue culture flasks that have been coated with 1.5% gelatin in PBS overnight.

7. The PMEC cultures are then incubated in a 5% $CO_2$, 95% humidified atmosphere at 37° C. The PMEC are routinely passaged at confluency using 0.02% trypsin in a $Ca^{2+}$ and $Mg^{2+}$-free PBS containing EDTA to dislodge the cells from the plate and to dissociate cell aggregates.

8. Cells to be transfected/infected are plated at a 1 to 4 split ratio onto 75 ml Corning tissue culture flasks that have been coated with 1.5%. gelatin in phosphate-buffered saline overnight. After an overnight incubation, the cells are transfected/infected as described above for CD59.
9. The genetically engineered endothelial cells can be frozen under liquid nitrogen and stored until needed.
10. To seed the genetically engineered cells into a cell network, the engineered cells are first dispersed in a 5 mg/ml solution of neutralized acid soluble type I collagen (isolated from calf dermis) at a concentration of $3.0 \times 10^6$ cells per ml of collagen solution at 4° C. This mixture is plated into 24-well cluster dishes in 0.75 ml aliquots and placed in a 37° C. incubator with a 5% $CO_2$, 95% air humidified atmosphere. Following gelation of the collagen, media is introduced over the gels. The cells are then cultured as above, refeeding the cells on a daily basis. After three days, the gels are scraped off the dishes using a sterile Teflon™ cell scrapper and transferred into Bellco™ four liter suspension culture vessels for one week and then frozen under liquid nitrogen and stored until needed.

In a preferred embodiment, the cells are engineered to result in the expression or production of molecules encoding therapeutic proteins or nucleotide molecules, respectively. Examples of therapeutic proteins include hormones, enzymes, receptors, immunomodulators, and neurotransmitters. Examples of therapeutic nucleotide molecule include antisense, ribozymes, and molecules binding to viral and bacterial nucleic acids to inhibit translation thereof. These capillary endothelial cell networks can then be implanted subcutaneously into a recipient patient, where the cells will secrete the therapeutic proteins systemically.

Because of their multi-level protection against the host's immune system, the engineered donor endothelial cells avoid graft rejection normally associated with the transplantation of non-autologous cells and thus can be used to administer their encoded therapeutic agent for substantial periods of time until, for example, removed from the host by a self-destruction mechanism of the type described above.

In a preferred embodiment, the genetically engineered capillary endothelial cells are seeded into a biological or synthetic matrix for implantation into the subcutaneous tissue of the recipient. The matrix may preferably be of commercially available biocompatible materials such as collagen types I through XII, thrombospondin, entactin, proteoglycans, glycosaminoglycans, vitronectin, laminin, fibronectin, fibrinogen, Matrigel™, or a combination of these and other natural extracellular matrix (ECM) components that allow capillary endothelial cells to form capillary networks in three dimensions since capillary endothelial cells, as opposed to large vessel endothelial cells or non-endothelial cells, form differentiated capillary networks in three dimensional collagen gels in vitro via the process of angiogenesis (Madri and Williams, "Phenotypic modulation of endothelial cells by transforming growth factor-beta depends upon the composition and organization of the cell matrix" *J. Cell Biol.* 106, 1375–1384 (1988)). The matrix is preferably in the form of a gel, prepared by modulation of matrix concentration, pH, temperature, salt content, or other physico-chemical properties known to those skilled in the art in order to induce gel formation. The gel matrix should be in a form suitable for seeding with cells and implantation into the body. There should also be sufficient porosity for diffusion of gases and nutrients prior to vascularization and, ideally, to allow anastamosis of recipient blood vessels to the donor capillary networks. It may be advantageous to add angiogenic factors to the matrix prior to, or at the time of, implantation. Such angiogenic factors will increase capillary network formation of the transplanted capillary endothelial cells and may also increase ingrowth of host capillaries. Other materials may serve as support structure for the three dimensional ECM gel such as ethylene vinyl acetate, polylactide-glycolide, polyanhydride, fibrous suture material, or other biocompatible synthetic polymers. The gel and, if present, the support structure, may be enclosed within a porous polymeric framework prior to implantation into the recipient.

As used herein, attachment molecules are any molecules for which there is a receptor on the cell surface. These include natural and synthetic molecules having one or more binding sites. Extracellular matrix molecules (ECM) include compounds such as laminin, fibronectin, thrombospondin, entactin, proteoglycans, glycosaminoglycans and collagen types I through XII. Other natural attachment molecules include simple carbohydrates, complex carbohydrates, asialoglycoproteins, lectins, growth factors, low density lipoproteins, heparin, poly-lysine, thrombin, vitronectin, and fibrinogen. Synthetic molecules include peptides made using conventional methods to incorporate one or more binding sites such as R G D from fibronectin, L I G R K K T SEQ ID NO.5 from fibronectin and Y I G S R SEQ ID NO.6 from laminin. Attachment molecules are bound to a surface by ionic or covalent binding, or by association (from solution or by drying). In some embodiments, the polymer may be modified to include one or more binding sites. Alternatively, the polymer may itself be formed in whole or in part by crosslinked attachment molecule or synthetic peptide.

The present invention will be more fully described by the following non-limiting examples.

EXAMPLE 1

Expression of Human CD59 in Porcine Endothelial Cells Protects them from Hyperacute Rejection by Human Complement This example demonstrates that when the full-length cDNA encoding the human CD59 protein is stably incorporated into the genome of a porcine aortic endothelial cell (PAEC) and expressed on the cell surface, it protects these cells from complement-mediated attack as assayed by human complement-mediated cell lysis in vitro.

Cultures of PAEC were cultured in DMEM containing 10% fetal bovine serum (FBS), 5 mM Hepes, 2 mM L-glutamine, and 1% each of penicillin and streptomycin (P/S). Prior to retroviral infection, the cells were grown to 50% confluence. Subconfluent PAEC were infected by using the amphotropic helper-free retroviral vector pRNSRalphaCD59+. The structure of this retroviral construct is shown in FIG. 1. As controls, PAEC were also infected with a control retroviral vector containing the drug selection marker gene neomycin or were uninfected. The amphotropic retroviral stocks were added to subconfluent cells growing in a T-25 tissue culture flask in a total volume of 3 ml. Polybrene was added to the flasks and the cultures were incubated at 37° C. for 2 to 5 hours. The cell culture media was then removed, monolayers were rinsed two times in 5 ml of media and then 5 ml of media was added to the cells which were incubated at 37° C. in 8% CO2.

Figure 2:
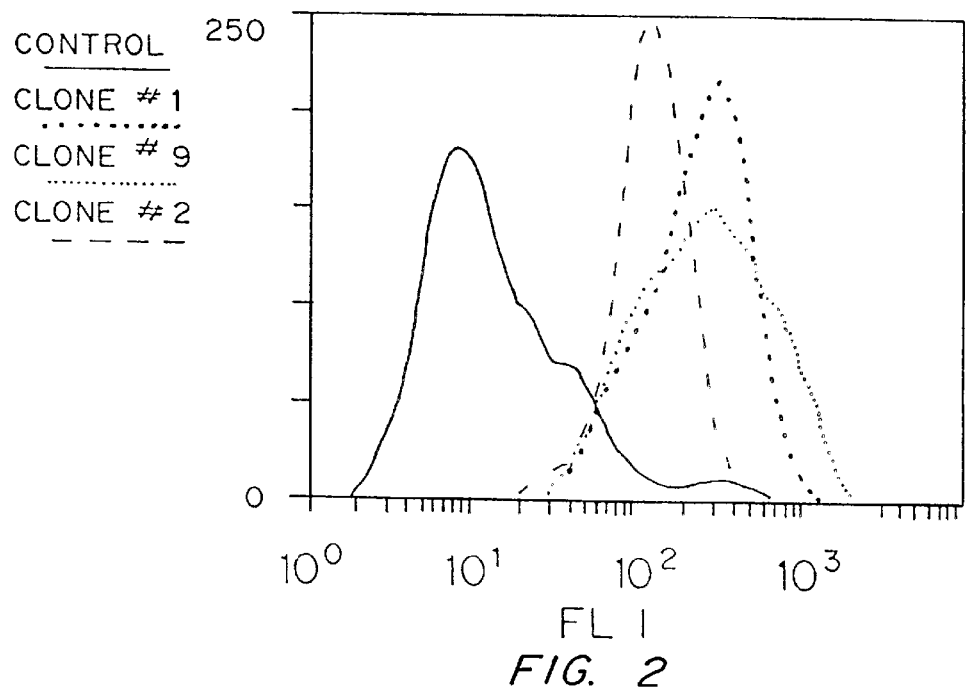
FIG. 2 is a graph of cell surface expression of human CD59 on porcine aortic endothelial cells (PAEC) as detected by anti-CD59 antibody and analyzed by flow cytometric analysis. The solid line represents the fluorescence intensity of PAEC infected with retrovirus shown in FIG. 1 carrying only the control neomycin resistance gene. The dashed line, small dotted line, and larger dotted line represent the fluorescence intensity of CD59-expressing PAEC cell clones 2, 9, and 1, respectively.
Figure 3A:
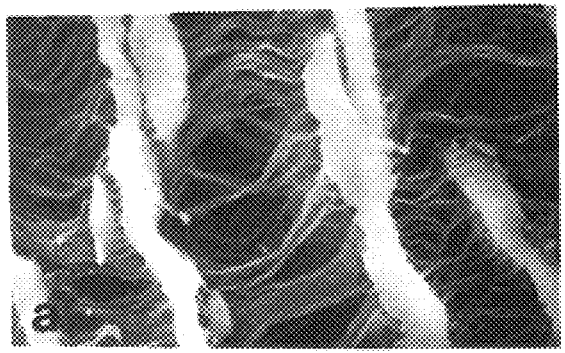
FIG. 3a is the control Gortex™, FIGS. 3b, c, and d are Gortex™ with CD59-expressing cells implanted thereon.
Figure 3B:
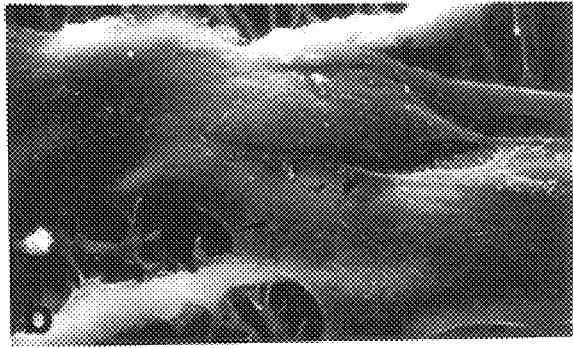
FIGS. 3(a–d) shows a scanning electron micrograph of CD59expressing PAEC attached to a synthetic Gortex™ graft.
Figure 3C:
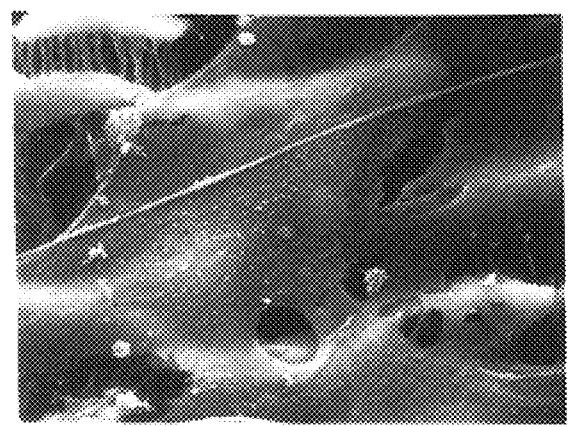
Figure 3D:
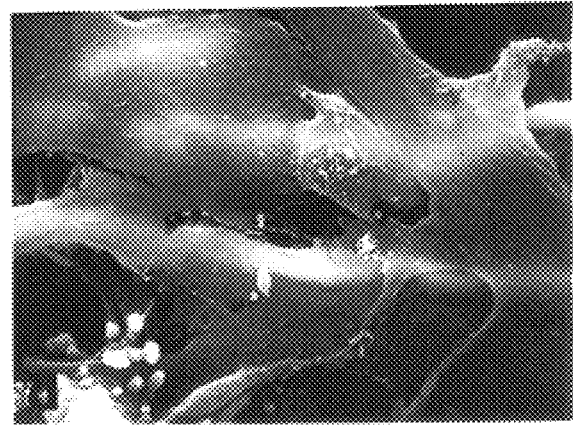

After a 24 to 48 hour incubation period, the cells were exposed to G418 (400 µg/ml) to select for stable integration of the retroviral construct. Neomycin resistant colonies were assayed for the cell surface expression of human CD59 by flow cytometric techniques (FACS analysis). To assess cell surface expression of human CD59 on porcine endothelial cells, confluent neomycin-resistant cell clones were grown to confluence in T-75 tissue culture flasks and cells were released for FACS analysis by incubation in Versene-EDTA for 10 minutes at 37° C. Harvested cells were pelleted via centrifugation and then resuspended in 2 ml of staining buffer containing phosphate-buffered saline (PBS), 0.2% sodium azide, and 2% FBS. Cells were then counted with a hemacytometer, pelleted by centrifugation, rinsed two times with staining buffer and then incubated for 30 minutes at 23° C. with a primary antibody to human CD59, either polyclonal rabbit anti-CD59 at 10 $\mu$g/ml or mouse anti-CD59 monoclonal 1F1 (obtained from Dr. Motowa Tomita, Showa University, Japan) at 1 $\mu$g/ml. The cells were then rinsed two times in staining buffer and then incubated for 30 minutes at 23° C. with an FITC-conjugated goat anti-rabbit IgG or an anti-mouse IgG diluted 1:50 in staining buffer. The cells were rinsed two times in staining buffer, once in PBS and then resuspended in 1% paraformaldehyde in PBS and analyzed by FACS. Positive cell surface expression of human CD59 (as measured by fluorescence intensity on the x axis) is demonstrated in FIG. 2 for cell clones 1, 2 and 9 but not for control PAEC infected with control containing only the neomycin resistance gene.

With regard to their biological behavior, the CD59-infected PAEC were not different from either uninfected PAEC or PAEC infected with control vector. For example, they maintained proliferation rates identical to uninfected cells and they did not overgrow monolayers or proliferate in suspension, and were contact inhibited. Additionally, CD59-infected porcine endothelial cells were capable of attaching to a synthetic Gortex™ graft, as demonstrated in the scanning micrograph shown in FIG. 3. Two centimeters square of synthetic Gortex™ sheets were steam-sterilized, placed in sterile 35 mm bacteriological petri dishes and overlaid with sterile stainless steel fences having a one centimeter square well. CD59-infected PAEC were then seeded into the center wells of the fences at a density of $1 \times 10^5$ cells in a volume of 0.5 ml of culture media as described above and incubated at 37° C. in 5% $CO_2$. After two days, the cultures were refed with media and after an additional two days the media was aspirated off and the cultures were washed with PBS and then fixed with buffered 2% glutaraldehyde, 4% paraformaldehyde for one hour. The fences were then removed and the Gortex™ was processed for scanning electron microscopy. FIG. 3 demonstrates that PAEC expressing cell surface human CD59 attach as well to synthetic GortexT grafts as normal endothelial cells.

Figure 4:
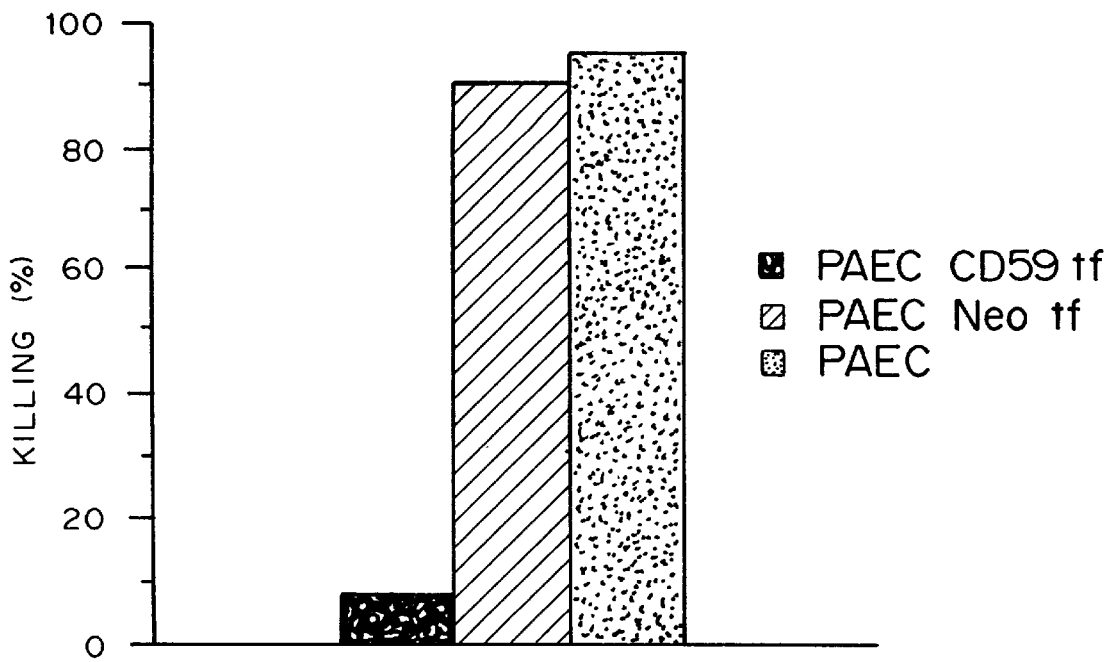
FIG. 4 is a bar graph showing the protection of human CD59-expressing PAEC from lysis by human complement. The solid bar represents the percentage of cell lysis of PAEC expressing human CD59. The cross-hatched bar represents the percentage of cell lysis of PAEC expressing only the control neomycin resistance gene while the stippled bar represents the percentage of cell lysis of control (noninfected) PAEC.

With regard to their biological activity, CD59-infected PAEC were assayed for their sensitivity to cytolysis by complement in human serum. To do this, CD59infected PAEC, control PAEC infected with vector alone, and uninfected PAEC were plated into 48-well tissue culture plates at a density of $1.25 \times 10^5$ cells/well in DMEM with 10% FBS, 2 mM glutamine and P/S. The culture media was removed and the cells were washed three times with media without FBS. Next, human serum diluted in DMEM at various concentrations was added to the cultures for 2 hours at 37° C. The percentage of viable cells remaining in the cultures was assessed by staining the cells with 0.1% trypan blue. FIG. 4 demonstrates that greater than 80% of uninfected or control (vector alone infected) PAEC were killed by human serum whereas less than 10% of CD59infected PAEC were killed. These results demonstrate that human CD59 expression on the surface of porcine endothelial cells protects these cells from the cytolytic activity of antibody and human serum, suggesting that in vivo these cells would be protected from complement-mediated hyperacute rejection.

The cells were then assayed to determine if the hCD59 would block complement activation, as well as the subsequent complement-mediated cell lysis. The following prothrombinase assay was used.

Prothrombinase:

Porcine aortic endothelial cells were stably infected with retroviral vectors carrying either a neomycin resistance gene alone (LXSN) or carrying human CD59 cDNA (LXSNCD59) or human CD59 cDNA engineered to carry a FLAG peptide epitope at its carboxy terminus (LXSNCD59Flg). These vectors were constructed from a defective Moloney murine leukemia virus. Ecotropic retrovirus was produced by transfecting Psi-2 cells with polybrene and selection in G418. Amphotrophic virus stocks were prepared by infecting Psi-AM packaging cells and stable transfectants were selected in G418 and assayed for there ability to form thrombin when challenged with human complement. Cells were incubated in C8-deficient human serum and then increasing concentrations of C8 were added to form the activating c5b-9 complement complex. Following incubation of the porcine cells with activating concentrations of human complement, bovine prothrombin, Factor Va, and Factor Xa were added to the final concentrations of 1.4 uM, 2 nM, and 10 pM, respectively. After a 6 minute incubation, aliquots were removed and the reaction terminated using EDTA. Thrombin generation was assayed using the synthetic substrate Spectrozyme TH (American Diagnostica, Greenwich, Conn.).

Figure 5:
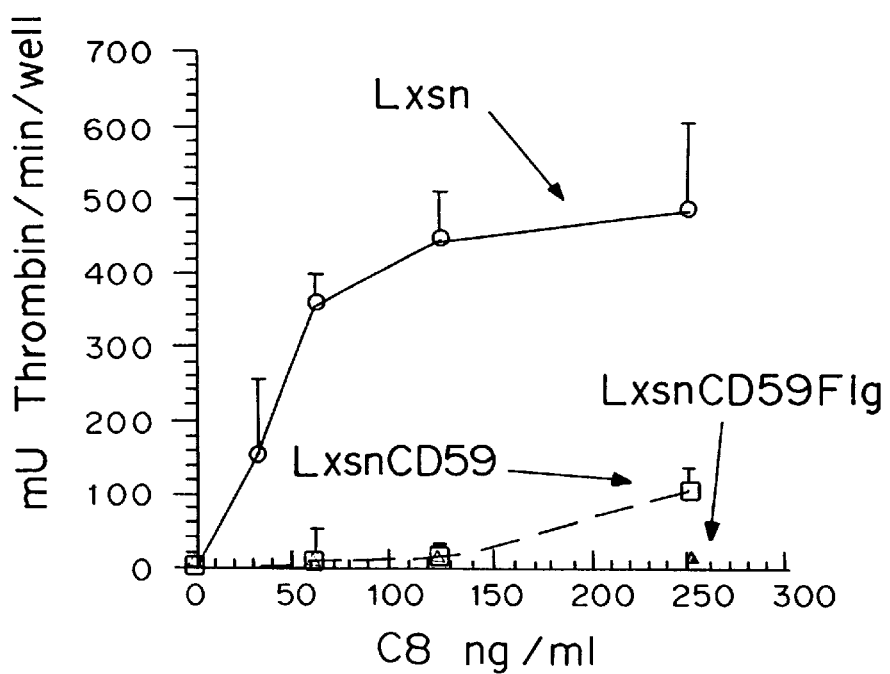
FIG. 5 is a graph demonstrating that hCD59 expressed on porcine endothelial cells blocks assembly of a prothrombinase complex, mU thrombin/min/well versus ng C8/ml, for Lxsn, Maloney leukemia virus-based retroviral vector without CD59 insert (open circles), LxsnCD59, vector with CD59 insert (open squares) (deposited with the American Type Culture Collection, Rockville, Md., ATCC Accession number 69336), and LxsnCD59Flg, vector with 5'Flg epitope-flagged CD59, ATCC Accession Number 69337, insert (dark triangles).

FIG. 5 is a graph demonstrating that hCD59 expressed on porcine endothelial cells blocks assembly of a prothrombinase complex, Lxsn, Maloney leukemia virus-based retroviral vector without CD59 insert (open circles), LxsnCD59, vector with CD59 insert (open squares), and LxsnCD59Flg, vector with 5'Flg epitope-flagged CD59 insert (dark triangles).

EXAMPLE 2

Figure 6:
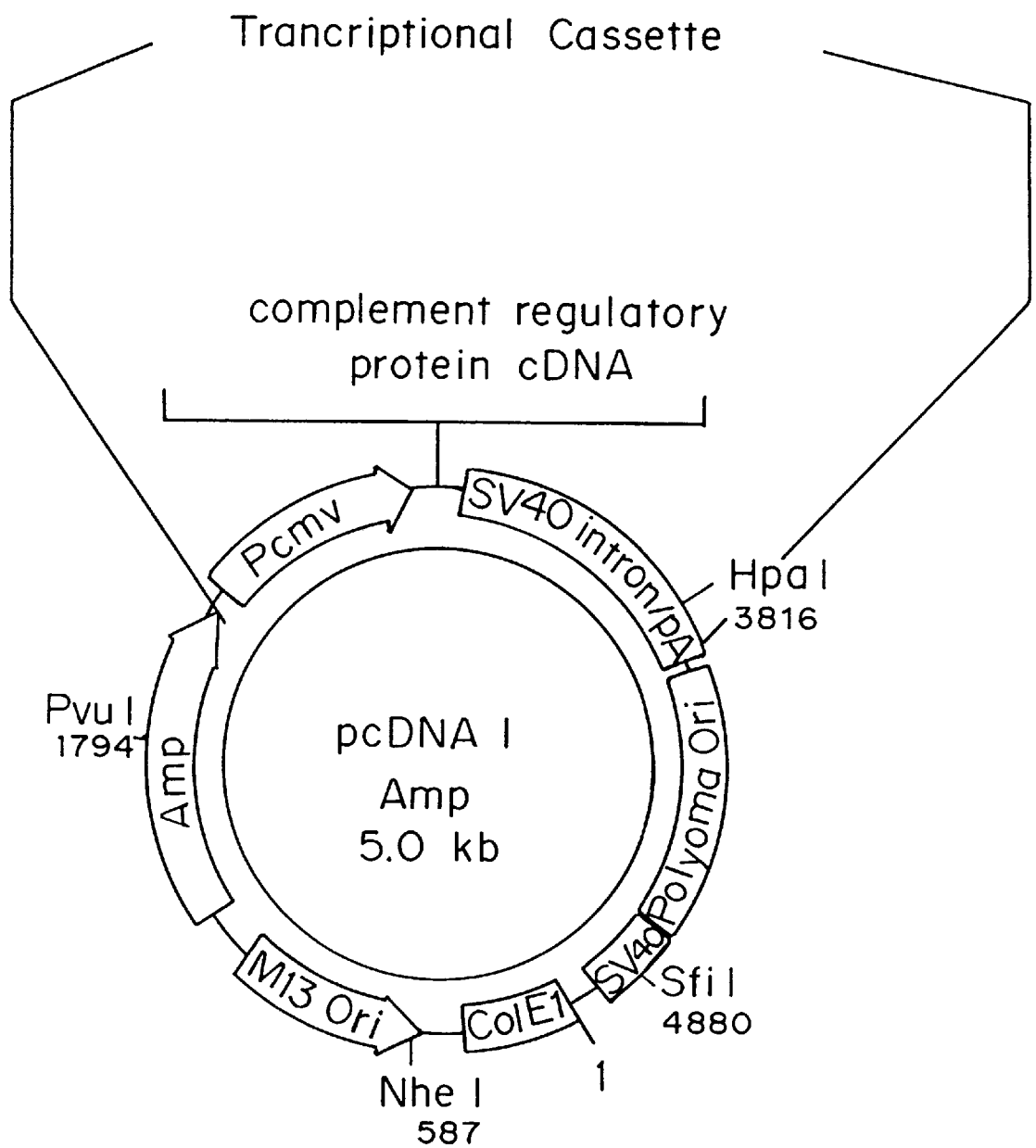
FIG. 6 is a schematic of the mammalian expression vector pcDNAI/Amp used to engineer transgenic mice expressing human CD59.

Stable Expression of hCD59 in Mouse Cells and which Protects the Cells from Complement Mediated Lysis Mouse Balb/3T3 cells were transfected with the pC8-hCD59-103 plasmid described in FIG. 6. The transfection was performed using the calcium phosphate precipitation method with 10 $\mu$g of plasmid pC8-hCD59-103 applied to approximately $10^6$ cells. Stable transfectants were selected by cotransfecting the Balb/3T3 cells with a neomycin resistance plasmid (pSV2-neo; Yale University, New Haven, Conn.; 1 $\mu$g per $10^6$ cells) and then selecting stably expressing cell clones in the presence of geniticin (G418; 500 $\mu$g/ml). Balb/3T3 cells transformed with just the neomycin resistance plasmid and not the pC8-hCD59-103 plasmid were used as controls.

Stable transfectants were assessed for hCD59 expression by flow cytometry using 10 $\mu$g/ml anti-CD59 monoclonal antibody MEM-43 (Accurate Chemical and Scientific Corp., Westbury, N.Y.) or 20 $\mu$g/ml of an anti-CD59 polyclonal serum (Southeastern Wisconsin Blood Center, Milwaukee, Wis.). The cells were incubated with the primary antibodies at 4° C. for 30 minutes. FITC-conjugated-anti-mouse IgG was then added and allowed to incubate an additional 30 minutes at 4° C. The cells were analyzed using a FACSort (Becton Dickenson) flow cytometer with the FL1 fluorescence channel (520 nm) set at logarithmic gain. The results show that stable transfection was achieved.

Positive hCD59-expressing Balb/3T3 clones were analyzed for the expression of functional CD59 by using a complement-dependent cell killing assay designed to monitor the cellular release of a fluorescent dye. The dye release assay was performed essentially as described by the manufacturer, Molecular Probes, Inc. (Eugene, Ore.). Briefly, the assay relies on the uptake of calcein-AM and its subsequent hydrolysis to the fluorescent calcein molecule. Calcein-AM is an esterase substrate that is membrane permeable and virtually non-fluorescent. Substrate hydrolysis by intracellular esterase activity yields the intensely fluorescent product, calcein. Calcein is a poly-anionic molecule that is retained in the living cell and results in the cell generating an intense uniform green fluorescence.

Complement-mediated dye release was determined from cell supernatants after incubation of the cells with a reactive antibody (polyclonal antiserum raised in rabbits to 3 types of mouse cells; L-cells, Balb/3T3 cells and MOP-8 cells, in the presence of complement C8-deficient human serum for 15 minutes at 37° C. EDTA-treated human serum was added back to the reaction at increasing concentrations (0–15%) for 30 minutes at 37° C. The percent dye release at the end of the incubation period was calculated from total uptake, corrected for non-specific dye release. Dye release was measured at 490 nm using a cytofluor fluorescence plate reader (Millipore).

The results demonstrate that the mouse Balb/3T3 cells which stably express human CD59 are protected from the complement killing effects of human serum whereas neomycin-resistant control clones not expressing hCD59 are sensitive to human serum-dependent cell killing.

EXAMPLE 3

Generation of Transgenic Mice Expressing hCD59

In order to achieve transgenic expression of hCD59, the CMV-hCD59-SV40 transcriptional unit was removed from pC8-hCD59-103 using the restriction enzymes SpeI and ScaI. This restriction digest selectively extracts the transcription unit from the overall vector and permits purification of only the essential elements required for expression.

The 2300 bp restriction fragment resulting from the digest was gel isolated, extensively purified through an ELUTIP column (Schleicher & Schuell, Keene, N.H.), dialyzed against pyrogen free injection buffer (10 mM Tris, pH7.4+ 0.1 mM EDTA in pyrogen free water), and used for embryo injection to generate transgenic mice in accordance with the methods of Hogan et al. 1986 and Brinster et al., 1985.

50 founder putative positive offspring were tested by harvesting genomic DNA from the tail of each of these animals. 5 micrograms of this genomic DNA from each of the 50 animals was transferred to nitrocellulose and dot-blot hybridization was performed using a $^{32}$P hCD59 cDNA probe generated from pUC19-hCD59 by cutting with BamHI and EcoRI. Varying amounts of CD59-pUC19 plasmid DNA served as positive controls for hybridization and copy number determination. Human genomic DNA isolated from the human choriocarcinoma cell line, Jar, was also used as a positive control.

Of the 50 founder offspring, 24 were determined to contain the transcriptional cassette of the invention. Transgene positive mice were then analyzed further for expression of hCD59 in various mouse cells and tissues.

Several cell and/or tissue types were isolated from the hCD59 transgenic mice in order to determine the extent of transgene expression in these transgenic animals. The initial analysis of each positive transgenic mouse involved isolating whole blood from the animal by retro-orbital bleeding. Clotting was prevented by the addition of ACD-2 (71.4 mM citric acid, 85 mM sodium citrate, 111 mM dextrose) at a ratio of 6 parts blood to 1 part ACD-2. The different cell types (i.e., erythrocytes, lymphocytes and monocytes) were analyzed for the presence of hCD59 on the cell surface using FACS. Erythrocytes were washed with HBSS+2% fetal calf serum and then processed directly. Total leukocytes were isolated from whole blood by hypotonic lysis of the erythrocytes followed by centrifugation and washing with HBSS+2% fetal calf serum.

Subsequent to washing, the cells were incubated in HBSS+2% fetal calf serum with the addition of 10 μg/ml anti-CD59 monoclonal antibody (MEM-43, Accurate Chemical and Scientific Corp., Westbury, N.Y.; or YTH53.1, Serotec, Indianapolis, Ind.) or 20 μg/ml of an anti-CD59 polyclonal serum (Southeastern Wisconsin Blood Center, Milwaukee, Wis.) for 30 minutes at 4° C. FITC-conjugated-anti-mouse IgG was added and allowed to incubate an additional 30 minutes at 4° C. The cells were then analyzed using a FACSort (Becton Dickenson) flow cytometer with the FL1 fluorescence channel (520 nm) set at logarithmic gain. One control monoclonal antibody, Y-3, specific for a common epitope shared by murine class I molecules H2Kb and H2Kk which represent the 2 possible haplotypes of the offspring, was used to assay erythrocytes for a known cell surface marker. Another antibody, T200, which recognizes the common leukocyte antigen CD45, was used as a control antibody to assess lymphocyte staining.

Flow cytometric analysis was performed on cells from several of the transgenic mice obtained as described above. This analysis showed that hDC59 was expressed on the monocytes of all of the CD59-positive transgenic animals tested. Litter mates negative for the hCD59 cDNA by Southern blotting did not express hCD59. Neutrophils and lymphocytes were negative for hDC59. These results demonstrate that hCD59 cDNA was expressed in transgenic animals.

Dissected tissues (i.e., abdominal aorta, heart, lung, and fat pad) from hCD59 transgenic animals and from negative litter mates were submerged in O.C.T. (Tissue Tek II, Miles, Elkhart, Ind.) and frozen in cryomolds. Tissue sections were cut on a cryotome and mounted on slides. Duplicate sections were then processed for immunohistochemistry. The tissue sections were stained with anti-CD59 antisera (MEM-43 or YTH 53.1) and anti-MHC Class I (Y-3, as a control), washed several times with PBS, and then incubated with an Rhodamine-conjugated goat anti-mouse IgG secondary antibody. Ausubel et al., *Current Protocols in Molecular Biology* Vol. 2, (Wiley Interscience, John Wiley and Sons 1987). Slides were viewed, scored visually as either CD59-positive or CD59-negative and photographed with a MRC-600 confocal microscope (Bio-Rad Laboratories, Richmond, Calif.).

The results of the immunohistochemical staining for abdominal aortic tissue demonstrate positive cellular expression of CD59 in the tissue section in the transgenic animals. The immunohistochemical stain reveals bright staining of the intimal layer of abdominal aortic endothelial cells and bright staining of the aortic adventitial capillary endothelial cells. Some low level staining of medial smooth muscle cells could be seen. Similar results were obtained for the other tissues tested. Bright staining of endothelial cells lining the coronary arteriolar region was observed, along with staining of myocardial cells. Reduced staining of alveolar epithelial cells was seen in combination with bright staining of adjacent capillary endothelial cells. For the mouse epididymal fat pad, which is an example of a systemic capillary network, there was bright capillary endothelial cell staining and present, but reduced, interstitial staining.

These tissue examinations demonstrate that the transcriptional cassette produces a high degree of endothelial cell expression of hCD59 in the transgenic mammal in both systemic and pulmonary circulations, and in capillary, arteriolar, and arterial vasculatures.

EXAMPLE 4

Generation of Recombinant Mice Bearing a Deletion of the Invariant Chain (li) Having Reduced Cell Surface MHC Class II Expression and Diminished Ability to Present Exogenous Protein Antigen Major histocompatibility complex (MHC) class I and class II molecules bind and present peptide antigen to T-cells. While class I molecules predominantly bind peptides generated from endogenously synthesized cytosolic proteins prior to their release from the endoplasmic reticulum (ER), class II MHC molecules present exogenously derived internalized antigen.

Class II molecules are expressed on the cell surface as heterodimers composed of a 34 kD $\alpha$ and 28 kD $\beta$ chains. The $\alpha$ and $\beta$ chains also interact with a third glycoprotein, the invariant chain (li), following their translocation into the ER. The $\alpha\beta$li complex is then transported through the Golgi apparatus to an acidic compartment where the li is proteolytically removed. It is within this same compartment that class II molecules may come in contact with exogenous antigens that have been internalized by endocytosis. Although many important features of this pathway remain unknown, it appears that a coordinated series of events may simultaneously generate both peptide antigens and li-free- $\alpha\beta$ dimers leading to class II-peptide interaction. Finally, class II $\alpha\beta$-peptide complexes are transported to the cell surface for presentation to antigen-specific T-cells.

Figure 7A:
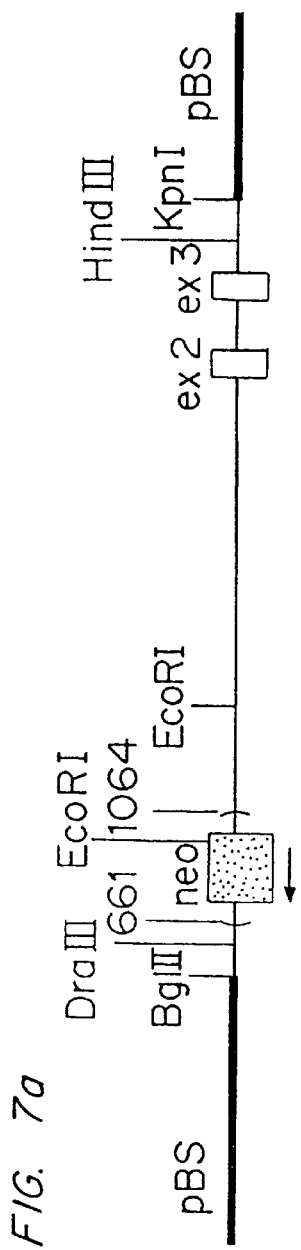
FIG. 7A shows a restriction digest map of the gene targeting vector for the mouse invariant chain gene cloned into pBS (Bluescript). The targeting vector contains the neomycin gene (neo).
Figure 7B:
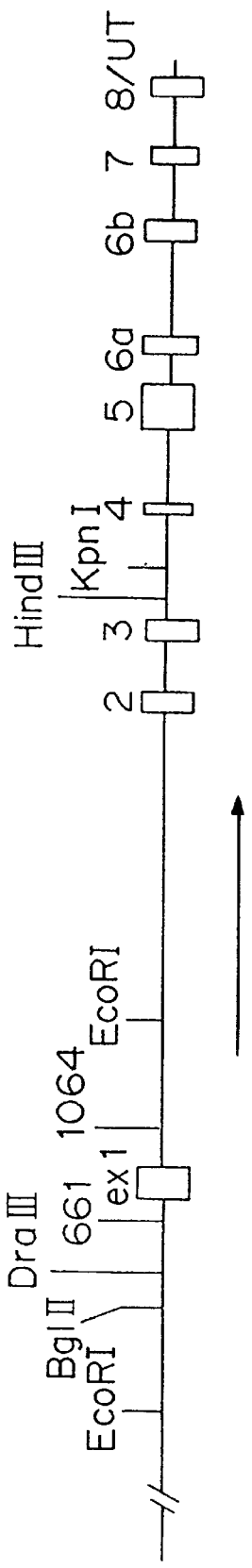
FIG. 7B shows a partial restriction digest map of the endogenous mouse invariant chain gene and FIG. 7C shows a restriction digest map of the disrupted invariant chain gene achieved by homologous recombination. Arrows indicate the direction of transcription in all three panels. The recognition region for the radiolabeled invariant gene probe used for the Southern blot shown in FIG. 8 is indicated by a solid bar below FIG. 7C.

This example demonstrates that the invariant chain gene can be disrupted in mouse embryonic stem cells (ES cells), and in transgenic mice produced using the ES cells, by specifically and stably replacing it in the genome with a mutated and non-functional form of the invariant chain gene and that replacement of the native invariant chain gene with a non-functional mutant can be achieved in a given cell by gene targeting technology which takes advantage of a homologous recombination event between the mutated gene and the native invariant chain gene. A partial restriction enzyme map for the mouse invariant chain gene is shown in FIG. 7B. Digestion of mouse genomic DNA with the restriction enzyme DraIII should generate an invariant chain gene fragment of approximately 8.7 kb when this DNA is probed by Southern blotting with a radiolabeled probe specific for the mouse invariant chain gene. This result is obtained and demonstrated in FIG. 8 (lane identified as parental cells).

To disrupt the mouse invariant chain gene by homologous recombination, a gene targeting vector was constructed, so as to replace a sequence of the invariant chain gene between nucleotides 661 and 1064 with the neomycin gene. This genetic engineering leads to the elimination of most of exon 1 including the translation initiation codon ATG, and a large portion of the promoter including the TATA box and CAAT box which function as regulatory elements required for accurate and efficient transcription of the invariant chain gene, as reported by Zhu and Jones, 1989 "Complete sequence of the murine invariant chain (Ii) gene" *Nucleic Acids Res.* 17:447–448. This gene targeting vector is shown in FIG. 7A as a general example of the disruption strategy. By deleting this region of the invariant chain gene, all expression of this gene including transcription and translation will be eliminated. As demonstrated below, deletion of li chain causes a significant reduction of cell surface class II expression, accumulation of class II molecules in the endoplasmic reticulum and a significantly diminished ability to present exogenous protein antigen. In vivo, li chain "knock-out" mice show a profound reduction in their CD4$^+$ T-cell subpopulation. These results demonstrate that the li chain is required for proper intracellular transport and normal regulation of class II restricted immune responses.

Replacement of the Native Invariant Chain Gene with the Mutated Invariant Chain Gene Replacement of the native invariant chain gene with the mutated invariant chain gene was first demonstrated in mouse embryonic stem cells. Embryonic stem cells (ES cells) were routinely passaged every other day in ES growth media containing DMEM (high glucose) with 15% FBS and 0.1 mM 2-mercaptoethanol. The ES cells were maintained on a confluent layer of primary embryonic fibroblasts. Two days prior to the transfection of the ES cells with the gene targeting vector the cells were expanded in culture. To transfect these cells, 25 $\mu$g of DNA corresponding to the invariant chain targeting vector were introduced into 1×10$^7$ ES cells by electroporation using a BioRad electroporator set at 250 MF and 0.32 kV. The ES cells were then seeded onto 10×100 mm Nunc™ tissue culture plates and stable transfectants were selected for chromosomal integration by way of neomycin resistance in G418 (170 $\mu$g/ml) and/or gangcyclovir in some experiments where the herpes-simplex virus thymidine kinase gene was included in the targeting vector.

Figure 7C:
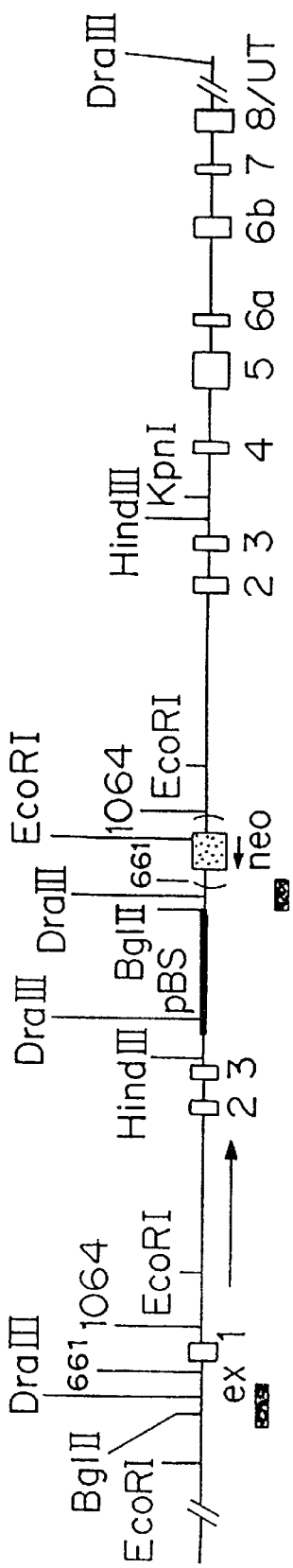
Figure 8:
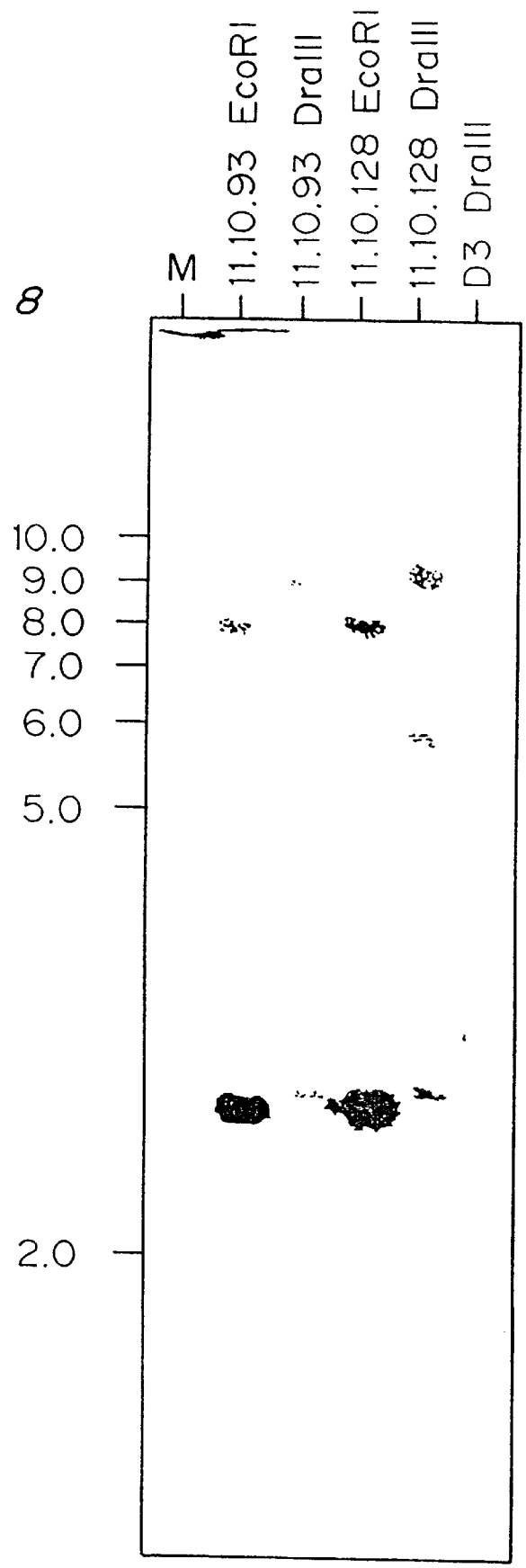
FIG. 8 is a Southern blot showing the restriction digestion pattern for two independent neomycin resistant mouse embryonic stem cell clones where the endogenous invariant chain gene has been disrupted by homologous recombination and replaced with a mutated form of the gene. The two clones are designated 11.10.93 and 11.10.128. Size markers are indicated on the left side. The DraIII restriction pattern of the parental cells is indicated in the far right lane and is clearly different from the restriction pattern of the two clones carrying the modified invariant chain gene.

After 14 days in selection media, individual neomycin resistant colonies were selected and propagated on feeder layers of confluent embryonic fibroblasts. Genomic DNA was isolated from 55 individual stable transfectants and digested overnight with either the EcoRI or DraIII restriction endonucleases. Digested DNA was resolved by electrophoresis, blotted to GeneScreen+™ nylon membranes and then hybridized with a radiolabeled DNA probe specific for the mouse invariant chain gene. The pattern of hybridizing bands for two independent clones, 11.10.93 and 11.10.128, shown in FIG. 8 is consistent with the mutant form of the invariant chain gene (where exon 1 was disrupted by the insertion of neomycin gene sequence) having homologously recombined and replaced the endogenous invariant chain gene. The pattern of restriction nuclease digestion observed is outlined diagrammatically in FIG. 7C. The frequency of recombination was determined to be 2 in 55 clones. These data, therefore, demonstrate that this targeting vector can disrupt the native cellular invariant chain gene.

Generation of Mice Deficient in Expression of the MHC Class II-associated li Gene by Introducing a Deletion into the li Gene of Embryonic Stem Cells Homologous recombination was used to generate mice deficient in expression of the MHC class II-associated li gene by introducing a deletion into the li gene of the embryonic stem cell line ES-D3, described by Doetschman, *J. Embryol. Exp. Morph.* 87,27–45 (1985). A 0.4 kb StuI fragment containing exon 1 and a portion of the li promoter region was replaced with a neomycin resistance (neor)

cassette to create an li targeting vector, pliKO, as shown in FIG. 8. The targeting vector contained 5 kb of homologous flanking sequence and two copies of the herpes simplex virus (HSV-1) thymidine kinase (tk) gene inserted at the 5' end of the li fragment. A 2.1 kb BglII-EcoRI fragment encoding the promoter and exon 1 was subcloned into pSK Bluescript (Stratagene, LaJolla, Calif.). The internal 0.4 kb StuI fragment was deleted and the neomycin resistance cassette (pMC1neo PolyA, Stratagene) was introduced in place of the StuI fragment. An additional 3.0 kb EcoRI-KpnI fragment encoding exon 2 and 3 was added to the 3' end of the BglII-EcoRI subclone. Finally, two copies of the HSV-1 thymidine kinase gene were subcloned into the NotI polylinker site 5' of the li gene. ES-D3 cells (1×10$^7$) in 0.7 ml of media were transfected with 25 µg of NotI linearized DNA with the Bio-Rad Gene Pulser (25 uF, 0.32 kV). Following electroporation the cells were plated on ten 100-mm plates in media (Dulbecco's modified Eagle medium with 15% fetal calf serum, 2 mM glutamine and 0.1 mM 2-mercaptoethanol) supplemented with leukemia inhibitory factor (Gibco-BRL). Media with geneticin (170 µg/ml; Gibco) and gancyclovir (2 µM; Syntex, Palo Alto, Calif.) was added 24 hours after transfection. All transfectants were maintained on a monolayer of 1° embryonic fibroblasts during the 10 day drug selection.

Figure 9A:
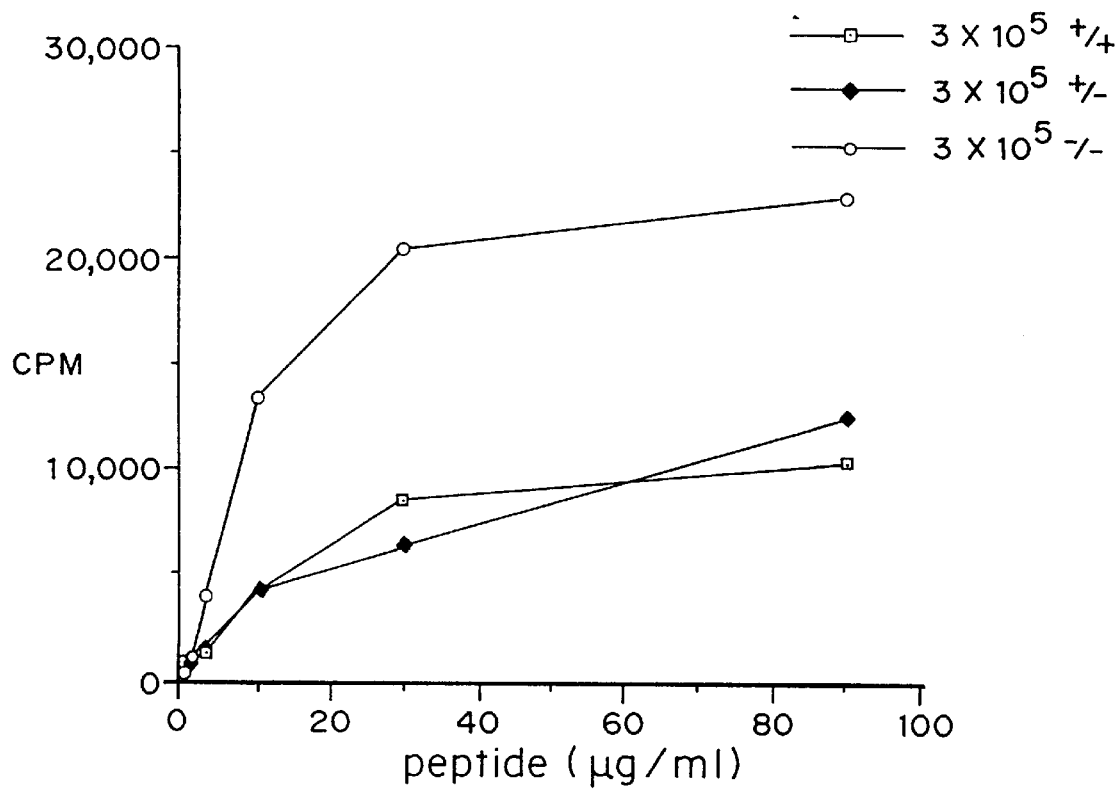
FIGS. 9a and 9b are graphs demonstrating splenocytes from mutant -/- mice are functional in presenting peptide antigens to T-cell hybrids but show diminished ability to present intact protein antigen, CPM versus peptide concentration (μg/ml) for concentrations of $3 \times 10^5$ of Eα 56–73 peptide (9a) and $1 \times 10^5$ of recombinant Eα S1/2 fusion proteins (9b) for +/+ (open squares); +/- (dark diamonds); and -/- (open circles).
Figure 9B:
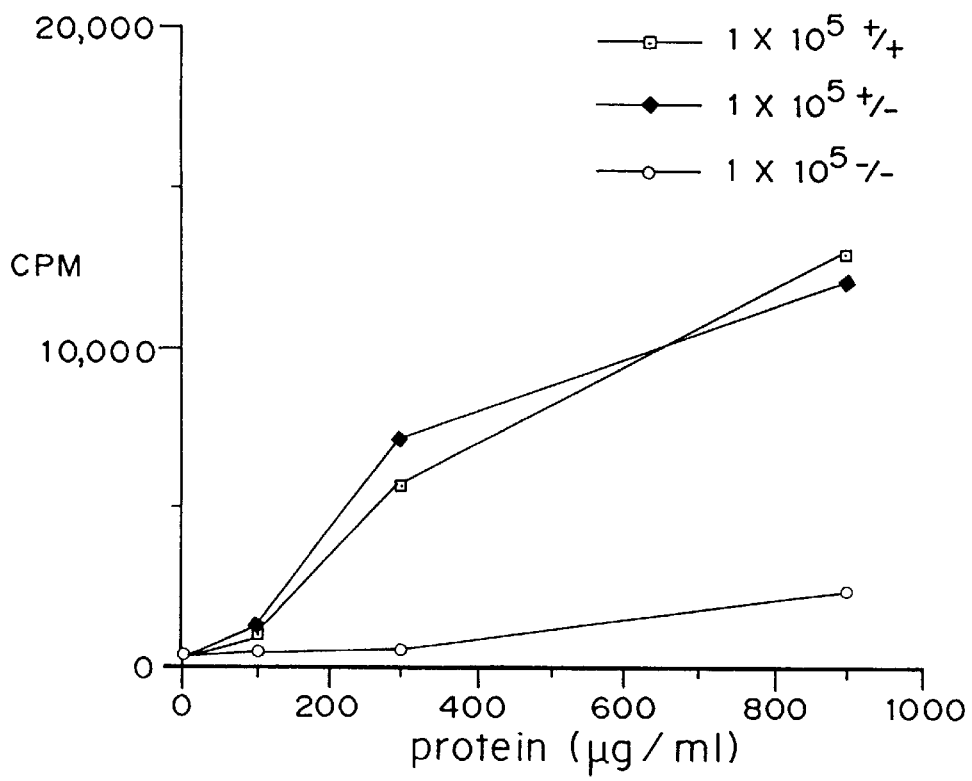

Genomic DNA was purified from individual clones and analyzed by Southern blot with a 5' probe indicated by the solid box, as shown in FIG. 9. This probe is a 0.6 kb BglII-XbaI fragment from the 5' end of the li gene. It hybridizes to a 3.0 kb EcoRI fragment of the endogenous li gene and to a 2.5 kb fragment of the disrupted allele. The Southern blot analysis is a hybridization of the li probe to EcoRI digested tail DNA from littermates derived from the mating of two heterozygous +/Δli mice. Hybridization with the 5' li probe identifies animals which are homozygous wildtype (+/+), heterozygous (±), or homozygous for the disrupted li allele (−/−). The 3.0 kb and 2.5 kb markers indicate the migration of the wildtype and mutated alleles, respectively. Insertion of the tk genes into the targeting construct allowed for positive-negative selection of the ES-D3 transfectants. A total of 1×10$^7$ ES=D3 cells were electroporated with the pliKO construct.

After selection, 1.4×10$^3$ G418-resistant colonies were recovered. of these, 3×10$^2$ transfectants were also resistant to gancyclovir. A total of 60 doubly resistant clones were tested by Southern blot analysis. Two clones were identified as having incorporated the targeting vector by homologous recombination. Both clones were tested with a series of restriction enzymes to confirm that they contained a single insertion of the targeting construct at the appropriate site. One clone, containing a disrupted li allele, was injected into C57BL/6 blastocysts. A total of 8 male chimeras were born and then bred. One of the male chimeras transmitted the ES cell genotype to 100% of its offspring. As determined by Southern blot analysis of tail DNA (FIG. 9), approximately one half of the offspring contained a disrupted li allele (±). Of the F2 animals derived from heterozygous brother×sister mating, one quarter of the progeny were homozygous for the li gene mutation (−/−).

To confirm the loss of li protein expression, the LPS-treated splenocytes from wildtype, heterozygous (+/−), or mutant (−/−) mice were examined by immunofluorescence confocal microscopy using the li-specific antibody, ln-1. Confocal microscopy of LPS treated splenocytes from heterozygous (±) and homozygous (−/−) was performed with an invariant chain specific antibody, ln-1. Splenocytes were attached to Alcian Blue coated cover slips, permeabilized with 0.01% saponin and stained with the invariant chain specific mAb ln-1 (A gift from Jim Miller, Chicago University) followed by affinity purified donkey anti-rat-TRITC (Jackson Labs). The cells were then imaged on either a Zeiss confocal microscope. The +/− splenocytes expressed normal levels of li as compared to C57BL/6 or 129Sv/J parental mice. As expected, no li expression was detected either on the plasma membrane or intracellularly in LPS-treated splenocytes from the −/− mice.

To determine whether the loss of li expression had any effect on the expression or transport of class II α and β chains, flow cytometric analysis of splenic lymphocytes was performed. Splenic single cell suspensions were made from individual wildtype (+/−) (dashed line) and mutant (−/−) (solid line) animals. 5×10$^5$ cells were stained with hybridoma supernatant containing either class II specific antibodies, M5/114 or alloantibodies, Y-Ae. The cells were washed twice with staining buffer (1×PBS, 1% fetal calf serum, 0.1% NaN$_3$) and incubated with the second step reagent fluorescein-conjugated mouse anti-rat antibody (M5/114) or fluorescein-conjugated F(ab')2 fragment of rabbit antibody to mouse IgG(Y-Ae). Finally, the cells were washed, fixed with 1% paraformaldehyde and analyzed by flow cytometry on a Becton Dickinson FACS Star. In addition to M5/114 other class II specific Ab (Y3P, Y248, Y219, AF120.6, and Y237) were used to stain splenocytes. All antibodies tested gave similar results.

To determine whether the reduced cell surface expression of class II molecules in the −/− mice was due to an inability of α and β chain to be transported out from the ER, the intracellular distribution of class II molecules was determined by immunofluorescence confocal microscopy. LPS-treated splenocytes were double-labeled for class I and various antigenic markers known to be localized to distinct organelles. LPS stimulated splenocytes were attached to Alcian Blue coated cover slips, permeabilized with 0.01% saponin and stained with primary antibody and affinity purified secondary antibody. The cells were then imaged on a Zeiss confocal microscope with either staining with a Rabbit anti-serum raised to affinity purified I-A$^d$ (Rb anti-I-A$^d$, a gift of Dr. Ralph Kubo, Cetus, Corp., LaJolla, Calif.) and affinity purified FITC-goat anti rabbit; staining with Rb anti-I-A$^d$ (Green) and the FcR specific mAb 2.4G2 (Red), or staining with Rb anti-I-A$^d$ (Green) and an anti-BiP mAb (Red). As detected by a panel of monoclonal antibodies (mAb) specific for either Aβ$^b$ or Aα$^b$, splenocytes from the homozygous mutant mice exhibited a 5–10 fold reduction in the level of class II staining on the plasma membrane. Relative to the staining observed in splenocytes from parental or heterozygous (±) mice, class II molecules in cells isolated from homozygous −/− mice exhibited a diffuse intracellular distribution suggestive of a predominant localization to the ER. Although this was evident from the singly-stained images, the intracellular localization of class I molecules in the −/− cells was directly illustrated by co-staining with a plasma membrane marker (Fc receptor; FcγRII). In the −/− splenocytes, cells were often observed in which class I staining (FITC) appeared as a concentric ring contained within the surface staining due to the FcγRII (TRITC). In ± splenocytes, FcγRII and class II staining co-localized.

That the internal class II staining in the −/− cells might reflect an ER localization was suggested by double staining with antibodies to BiP. In cells from +/− or parental mice, when BiP staining was evident (TRITC), it was always distinct from and contained within a larger ring-like surface fluorescence due to plasma membrane class II molecules (FITC). On the other hand, in cells from −/− mice, many cells exhibited significant overlap between the two staining patterns (appearing as yellow in the confocal images). Not all cells exhibited interpretable patterns due to the low cytoplasmic content of the splenocytes. Moreover, in LPS-treated splenocytes, cells exhibiting high levels of class II expression generally exhibit low levels of BiP expression, and vice versa. Since no overlap was observed in the −/− cells between class II staining and staining for mannosidase II (medial Golgi), TGN38 (trans-Golgi), or lgp 120 (lysosomes), these experiments strongly suggest that in lymphocytes, li is required for efficient transport out from the ER.

Figure 10:
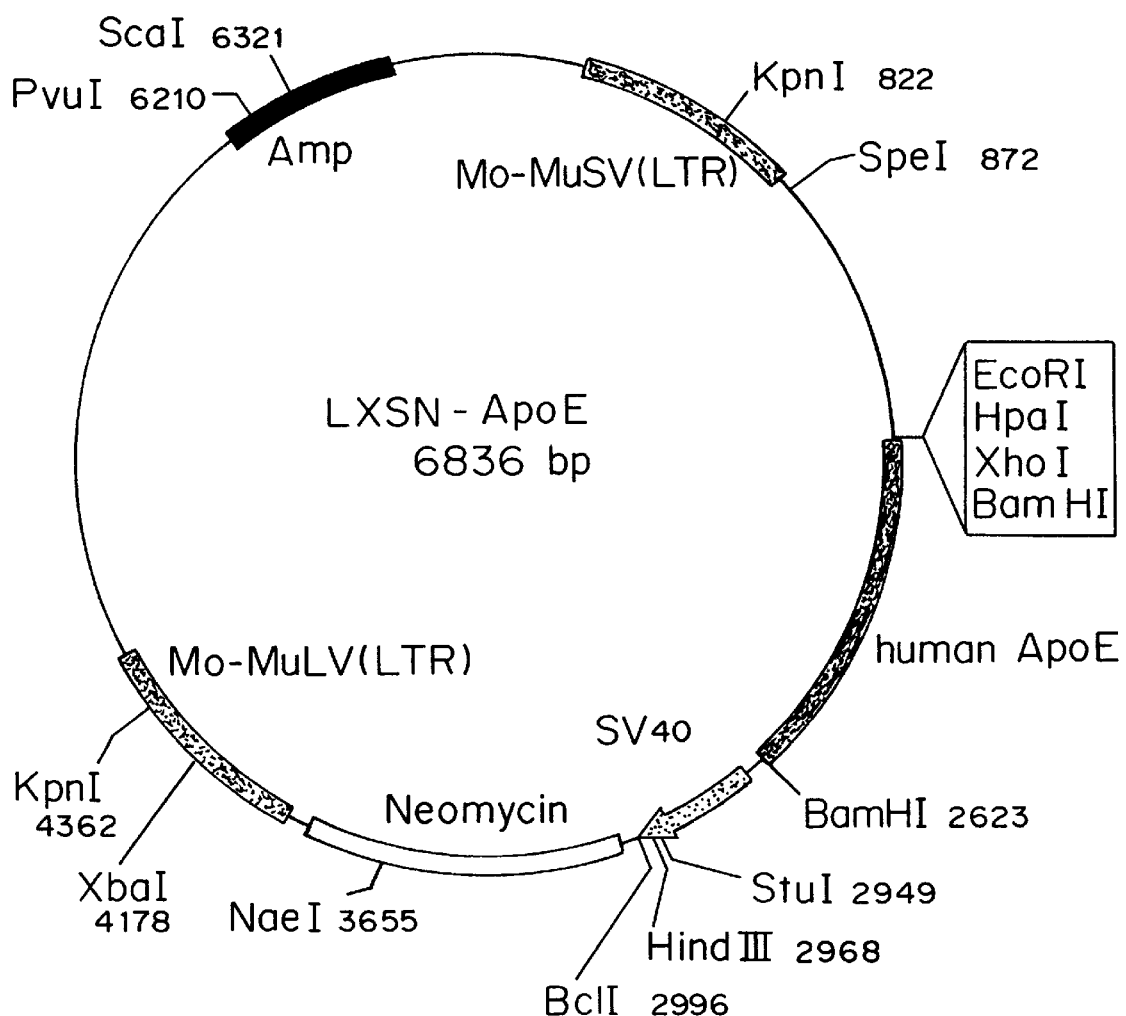
FIG. 10 is a schematic of the retroviral vector used in Example 5. This vector was constructed from a defective Moloney murine leukemia virus. A cDNA fragment encoding the full-length and functional human apolipoprotein E (Apo E) was subcloned into the retroviral vector. The resulting plasmid was designated Lxsn-ApoE, ATCC Accession Number 69335. Ecotropic retrovirus was produced by transfecting Psi-2 cells with polybrene and selecting in G418. Amphotrophic virus stocks were prepared by infecting Psi-AM packaging cells and stable transfectants were selected in G418.

Since some class II molecules could be detected on the surface of −/− splenocytes, the requirement for li in the exit of class II molecules from the ER is not absolute; moreover, it is evident that α and β chains that do exit the ER can reach the cell surface. To test whether these molecules were properly folded and functional, it was determined if they were capable of presenting peptide or protein antigens to a panel of antigen-specific T-cell hybridomas. Mutant and control cells were tested for their ability to process/present Eα 56–73 peptide, as shown by FIG. 10a, and recombinant Eα S1/2 fusion proteins, as shown by FIG. 10b, to T-cell hybrids. These are described by Rudensky, et al., Nature 353, 660–662 (1991) and 622–627 (1991). Mutant splenocytes (open circles) are far better at presenting exogenous peptide antigens then are the control +/+ (open squares) or ± (dark diamonds) cells. In contrast the −/− cells are at least 10 times less efficient at presenting Eα fusion protein. No stimulation of the T-cells was observed when a non-relevant fusion protein, Conpep (described by Nakagawa, et al., Eur. J. Immun. 21, 2851–2855 (1991), was substituted for the EαS1/2 protein. Stimulation of the T-cell hybrids was measured by incubating 1×10$^5$ 1H$_{3.1}$ hybrid cells (Rudensky, 1991) with 1 or 3×10$^5$ spleen cells per well of 96-well plates in the presence or absence of peptide/protein. After 24 hour of incubation 50 μl aliquots of supernatants were removed and tested for lymphokine production using the CTLL-2 cell line at 5×10$^3$ cells per well. Cells were pulsed for 4 hours with 1 μCi per well of $^3$H-thymidine and collected. The Eα recombinant fusion protein was generated by subcloning oligonucleotides encoding the nucleotide sequence of the naturally processed Eα-derived 17mer peptide (Eα 56–73) into the BamHI site of pGEXTAG (Nakagawa, et al. 1991). The EαS1/2 fusion protein has a stop codon incorporated into the oligonucleotide such that the TAG peptide is not translated. Recombinant fusion proteins were expressed and purified as described by Smith and Johnson, Gene 67, 31–40 (1988). A nonspecific fusion protein, conpep, which encodes a conalbumin 13 amino acid peptide (amino acids 134–146) was produced and used to establish specificity of the T-cell response.

In summary, as shown in FIG. 10A, both the mutant and wildtype splenocytes are able to functionally bind and present exogenously added Eα peptide to an Eα specific T-cell hybridoma. However, the ability of the −/− cells to present intact Eα-containing fusion protein was markedly reduced as compared to +/+cells, as shown by FIG. 10B.

Since the li deficient mice were generated by targeted mutation of the li gene, −/− cells should not be defective at internalizing or degrading exogenous protein into antigenic peptides. Thus, the inability of mutant cells to present whole protein was likely to reflect a failure of the class II molecules to acquire processed peptide antigens either due to the inability of the α and β chains to reach to the appropriate endosomal compartment or their inability to bind processed antigen. If the class II molecules on the cell surface of −/− cells were transported from the ER to the cell surface without passing through a putative processing compartment, the peptide binding groove of the class II molecules might be "empty." To test this possibility, the ability of ± and −/− splenocytes to bind Eα peptide by measuring cell surface staining with Y-Ae was compared. Y-Ae is a monoclonal alloantibody that detects a determinant expressed on a subset of class II I-A$^b$ molecules when complexed with an Eα-derived peptide Eα56–73.

Mutant and wild type splenocytes were incubated with Ea peptide for 4 hr and then stained for the Y-Ae determinant. Both ± (dashed line) and −/− (solid line) cells expressed the Y-Ae epitope. However, the −/− cells showed a substantially higher degree of staining with Y-Ae Ab than did the =/− cells, consistent with our prediction that a greater fraction of surface class II molecules on −/− cells were "empty" and therefore capable of binding a greater amount of Eα peptide. This is also consistent with the antigen presentation results in which the mutant −/− cells were found to present the exogenous peptide better than the control cells. Similar results were obtained in at least one experiment in which the ability of class II molecules to present peptide antigen was determined in L-cells transfected in the absence of li.

EXAMPLE 5

Genetic Engineering of Microvascular Capillary Endothelial Cells, Implantation, and Expression of Protein in Vivo Isolation of Rat Microvascular Capillary Endothelial Cells.

Rat microvascular capillary endothelial cells were isolated by first removing the epididymal fat pads using sterile technique. The fat pads were placed in sterile HEPES (pH 7.4) which contains 140 mM NaCl, 10 mM HEPES, 10 mM KCl, 0.1 mM CaCl$_2$, 0.2 mM MgCl$_2$, 11 g/l NaHCO$_3$, 5.0 g/l glucose, 100 U/ml penicillin, and 100 U/ml streptomycin. The fat was then minced for 3 to 5 minutes with a scissors. The minced tissue was placed into flasks containing equal volumes of sterile HEPES buffer with 5 mg/ml collagenase and 5 mg/ml bovine serum albumin. The incubation was continued until the majority of the minced tissue contained tube-like fragments and single cells. The cell suspension was then centrifuged at 200×g for 7 minutes in 15 ml conical tubes. The top white fatty layer was then aspirated off and the pellets resuspended in 10 ml of HEPES buffer containing 10% BSA and recentrifuged and resuspended an additional two times. The resultant pellets were resuspended in 45% Percoll and centrifuged at 15,000×g for 20 minutes at 4° C. in a SS34 fixed angle rotor. The tufts of the RFCs are in a milky white layer beneath the top-most adipocyte-containing layer and above a translucent layer containing large vessel fragments. The tufts were resuspended in media (Medium 199E containing 20% heat inactivated fetal bovine serum, 5 mM HEPES, penicillin and streptomycin, 5 mM pyruvate, and 5 mM glutamate mixed with 1:1 with the same medium containing 10% FBS which has been conditioned for 48 hours by incubating over confluent endothelial cells). The cells were then seeded into tissue culture flasks that have been coated with 1.5% gelatin in PBS overnight. The microvascular endothelial cell cultures were incubated in 5% CO2 at 37° C.

Genetic Engineering of Rat Microvascular Capillary Endothelial Cells for the Expression of Human ApoE Cells to be retrovirally infected were plated at a 1:4 split ratio onto 75 ml Corning flasks that had been coated with 1.5% gelatin. Retroviral vectors for the expression of human ApoE were constructed from a defective Moloney murine leukemia virus. A cDNA fragment encoding the full-length and functional human apolipoprotein E (Apo E) was subcloned into the retroviral vector. The resulting plasmid was designated Lxsn-ApoE. Ecotropic retrovirus was produced by transfecting Psi-2 cells with polybrene and selecting in G418. Amphotrophic virus stocks were prepared by infecting Psi-AM packaging cells and stable microvascular capillary endothelial cell transfectants were selected in G418.

Establishment of Three Dimensional Capillary Networks Expressing Human ApoE Protein To seed the genetically engineered cells into a capillary cell network, the engineered cells were first dispersed in a 5 mg/ml solution of neutralized acid-soluble type I collagen (isolated from calf dermis) at a concentration of $3.0 \times 10^6$ cells per ml in DMEM with 10% fetal calf serum and 25% bovine aortic endothelial cell-conditioned media. The cells were maintained at 37° C. with 5% $CO_2$. To assess expression and secretion of human ApoE protein, the media was harvested and analyzed by Western blot analysis using an antibody specific for human ApoE.

The analysis shows that rat epididymal fat pad capillary endothelial cells stably infected with the retroviral construct and cultured in a three dimensional collagen matrix express and secrete human ApoE as determined by Western blotting analysis using an antibody to human ApoE protein.

Despite the fact that the microvascular capillary cells have undergone a phenotypic change during their formation of capillary networks in three dimensional collagen gels, they continue to express and secrete levels of human ApoE equivalent to that of cells maintained in two dimensional cultures.

Transplantation of Three Dimensional Capillary Networks Expressing Human ApoE Protein The three dimensional capillary network in the collagen gels were injected subcutaneously into the flank of a rat. Five weeks after transplantation, these grafts were recovered and examined histologically. Histologic sections of genetically engineered rat epididymal fat pad capillary endothelial cells packaged in a collagen matrix which was then transplanted into the subcutaneous tissue of a recipient syngeneic rat show the presence of erythrocytes derived from the recipient circulating within the transplanted capillary endothelial cell collagen matrix graft, indicating functional vascular anastomosis between the recipient and the graft.

A variety of modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. An isolated non-human mammalian cell expressing a nucleotide molecule which codes for human CD59 and expressing a nucleotide molecule which codes for a protein inhibiting complement mediated attack of said cell, the protein selected from the group consisting of human CD55 and CD46.

2. The cell of claim 1 wherein the cell expresses CD55.

3. The cell of claim 1 wherein the cell expresses CD46.

4. The cell of claim 1 wherein said cell is selected from the group consisting of endothelial cells, fibroblasts, epithelial cells, skeletal, cardiac and smooth muscle cells, hepatocytes, pancreatic islet cells, bone marrow cells, astrocytes, and Schwann cells.

5. The cell of claim 1 further comprising a nucleotide molecule which is expressed by the cell and which codes for bacterial cytosine deaminase.

6. The cell of claim 1 wherein the cell is selected from the group consisting of cells of bovine origin and cells of porcine origin.

7. A prosthesis for implantation having cells according to claim 1 attached thereto, said cells being resistant to complement mediated attack.

8. The prosthesis of claim 7 wherein the prosthesis is a vascular graft.

9. The prosthesis of claim 7 wherein the prosthesis is a stent.

10. A method for re-endothelializing a blood carrying vessel selected from the group consisting of denuded blood vessels, stents, and vascular grafts comprising applying to the vessel cells according to claim 1, said cells being resistant to complement mediated attack, thereby allowing re-endothelialization of said vessel.

11. A transgenic non-human mammal comprising cells expressing a nucleotide molecule which codes for human CD59 and expressing a nucleotide molecule which codes for a protein inhibiting complement mediated attack of said cells, the protein selected from the group consisting of human CD55 and CD46, wherein the CD59 and, CD55 or CD46 are expressed in an amount effective to inhibit complement mediated attack of the cells when introduced into a human.

12. An organ from a transgenic non-human mammal, the organs formed of cells expressing a nucleotide molecule which codes for human CD59 and expressing a nucleotide molecule which codes for a protein inhibiting complement mediated attack of said cells, the protein selected from the group consisting of human CD55 and CD46, wherein the CD59 and, CD55 or CD46 are expressed in an amount effective to inhibit complement mediated attack of the cells when introduced into a human.

13. An isolated non-human mammalian tissue comprising non-human mammalian cells, the cells expressing a nucleotide molecule which codes for human CD59 and expressing a nucleotide molecule which codes for a protein inhibiting complement mediated attack of said cells, the protein selected from the group consisting of human CD55 and CD46, wherein the CD59 and, CD55 or CD46 are expressed in an amount effective to inhibit complement mediated attack of the cells when introduced into a human.

14. The tissue of claim 13 wherein the cells express CD55.

15. The tissue of claim 13 wherein the cells express CD46.

16. The tissue of claim 13 comprising cells selected from the group consisting of endothelial cells, fibroblasts, epithelial cells, skeletal, cardiac and smooth muscle cells, hepatocytes, pancreatic islet cells, bone marrow cells, astrocytes, and Schwann cells.

17. The tissue of claim 13 comprising cells selected from the group consisting of cells of bovine, and porcine origin.

* * * * *